US012575781B2

(12) United States Patent
Cotton

(10) Patent No.: US 12,575,781 B2
(45) Date of Patent: Mar. 17, 2026

(54) PORTABLE AND WEARABLE ELECTROMYOGRAPHIC BIOFEEDBACK FOR SPINAL CORD INJURY TO ENHANCE NEUROPLASTICITY

(71) Applicant: Rehabilitation Institute of Chicago, Chicago, IL (US)

(72) Inventor: Ronald Cotton, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 598 days.

(21) Appl. No.: 16/588,202

(22) Filed: Sep. 30, 2019

(65) Prior Publication Data

US 2020/0100692 A1     Apr. 2, 2020

Related U.S. Application Data

(60) Provisional application No. 62/738,774, filed on Sep. 28, 2018.

(51) Int. Cl.
*A61B 5/30*        (2021.01)
*G06F 3/01*        (2006.01)

(52) U.S. Cl.
CPC .............. *A61B 5/30* (2021.01); *G06F 3/015* (2013.01); *A61B 2505/09* (2013.01); *A61B 2560/0475* (2013.01); *A61B 2562/0219* (2013.01); *A61B 2562/0223* (2013.01)

(58) Field of Classification Search
CPC .................. A61B 5/30; A61B 2505/09; A61B 2560/0475; A61B 2562/0219; A61B 2562/0223; A61B 5/389; A61B 5/486; A61B 5/6898; A61B 2560/0468; G06F 3/015; G06F 3/0346
See application file for complete search history.

(56) References Cited

U.S. PATENT DOCUMENTS

| | | | |
|---|---|---|---|
| 6,413,190 B1* | 7/2002 | Wood .................. | A61B 5/1107 |
| | | | 482/8 |
| 10,327,674 B2* | 6/2019 | Hong ................. | A61B 5/02433 |
| 10,413,230 B1* | 9/2019 | Berme ................. | G06T 19/006 |
| 2007/0130893 A1* | 6/2007 | Davies ................. | A61B 5/1123 |
| | | | 54/1 |
| 2016/0066836 A1* | 3/2016 | Schneider ............ | A61B 5/0022 |
| | | | 600/546 |
| 2016/0077547 A1* | 3/2016 | Aimone ................ | A61B 5/1114 |
| | | | 345/8 |
| 2017/0164876 A1* | 6/2017 | Hyde .................... | A61B 5/1118 |
| 2017/0285756 A1* | 10/2017 | Wang .................... | G06F 3/0346 |
| 2017/0296048 A1* | 10/2017 | Lahiri .................... | A61B 5/318 |
| 2019/0339766 A1* | 11/2019 | Erivantcev ............. | G06V 40/20 |
| 2020/0178885 A1* | 6/2020 | Orr .......................... | A61B 5/00 |

* cited by examiner

*Primary Examiner* — Charles A Marmor, II
*Assistant Examiner* — Severo Antonio P Lopez
(74) *Attorney, Agent, or Firm* — Polsinelli PC

(57)        ABSTRACT

Various embodiments of a platform for providing electromyographic biofeedback are disclosed. The platform includes a sensor device having an IMU and electrodes for simultaneous tracking of IMU and EMG activity. The IMU and EMG data may be generated and leveraged in conjunction with a gaming application provided to a user while engaged to the sensor device to provide biofeedback therapy for rehabilitation.

24 Claims, 21 Drawing Sheets

PORTABLE AND WEARABLE ELECTROMYOGRAPHIC BIOFEEDBACK FOR SPINAL CORD INJURY TO ENHANCE NEUROPLASTICITY

CROSS REFERENCE TO RELATED APPLICATIONS

This is a non-provisional application that claims benefit to U.S. provisional patent application Ser. No. 62/738,774 filed on Sep. 28, 2018, which is herein incorporated by reference in its entirety.

FIELD

The present disclosure generally relates to systems and methods for neurological rehabilitation; and in particular, to a portable platform with a wearable sensor device that generates feedback suitable for improving spinal injury rehabilitation.

BACKGROUND

Electromyographic biofeedback has been shown to enhance recovery of muscle control for subjects with incomplete spinal cord injury. In the rehabilitation setting, tracking biofeedback can provide outcome scores, recovery metrics, and other useful information for tracking and managing recovery. However, its adoption is hindered based on current requirements for expensive equipment, trained personnel, and a laboratory setting.

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Various embodiments of a platform for providing electromyographic biofeedback are disclosed. In some embodiments, the platform described herein includes at least one flexible sensor device that acquires both electromyographic and inertial measurements while a user activates muscles in the course of engaging a game or other application of a mobile computing device; and aspects of the game may be modified based on the measurements acquired. The present platform overcomes the shortcomings of past attempts to provide electromyographic biofeedback because the platform is portable and affordable and can be employed by subjects to self-dose biofeedback therapy. In some embodiments, advances in flexible and stretchable electronics are leveraged such that the sensor device is encapsulated in silicone with integrated electrodes interfacing to the skin via an adhesive hydrogel. The sensor device may be incorporated into the platform and/or may be in operable communication with a smartphone game (or other mobile application) allowing real-time biofeedback. The sensor device may run for several days and may be charged wirelessly. In addition, data from the platform may be transparently synchronized to a secure cloud device, and the data may produce stable measurements over time. Accordingly, the therapy provided by the platform incorporates both wireless technology and portable biofeedback. The platform may be configured to be sensitive enough to allow game control by a subject with paraplegia.

In some embodiments, the disclosed sensor device records both inertial measurement unit (IMU) and electromyographic (EMG) activity, and may run an efficient quaternion-based complementary filter that estimates the sensor orientation while correcting for estimate drift and constraining magnetometer estimates to only influence heading. In one embodiment, the difference in two sensor orientations may be used to estimate a joint angle, which can be further improved with joint axis estimation. In this manner, successful tracking of joint angle and muscle activity in a home environment can be realized with the sensor devices described and a smartphone or other such mobile computing device.

Figure 1:
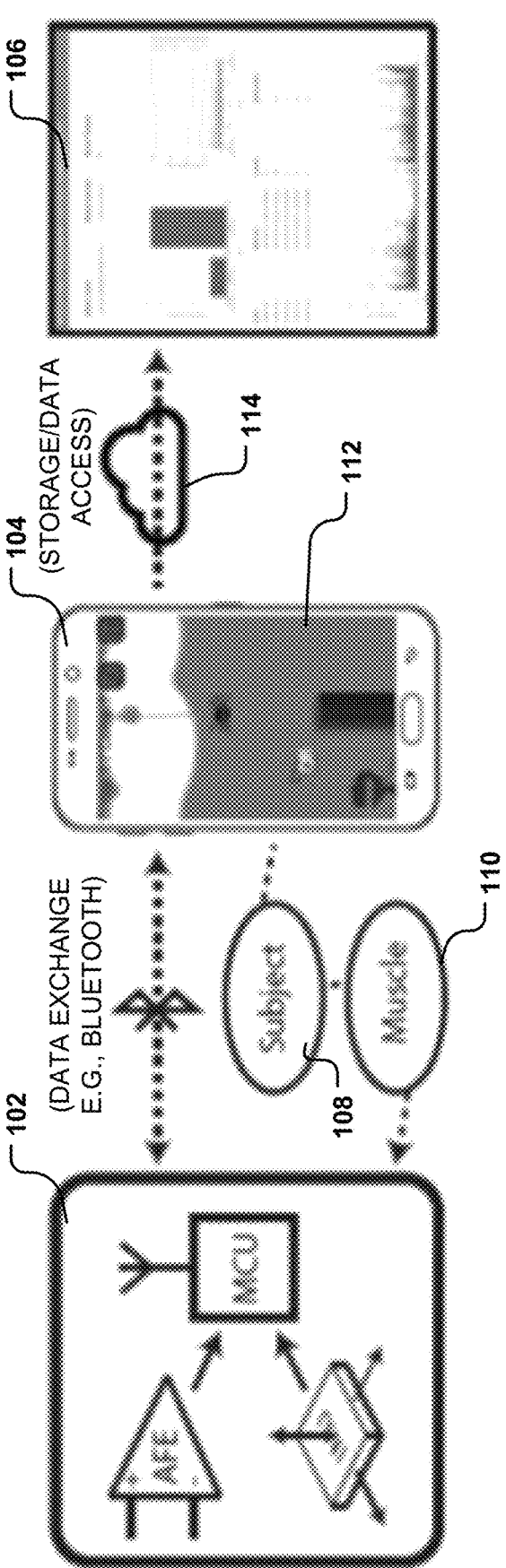
FIG. 1 is a simplified image illustrating an overview of one embodiment of a platform for providing electromyographic feedback as described herein.

Referring to FIG. 1, a platform 100 for providing portable biofeedback therapy is shown. As indicated, the platform 100 may generally include at least one of a wearable sensor device 102, and a mobile computing device 104 (e.g., tablet, laptop, or smartphone) which may be implemented to collectively generate biofeedback 106 or other useful information in the form of reports, logs, or other forms. In particular, the sensor devices 102 may generate EMG data and inertial measurements while a subject 108 or user activates a muscle 110 in the course of engaging a game or other application executed by the mobile computing device 104. The sensor device 102 may be low profile, wearable, flexible, and battery powered and may produce high quality surface EMG recordings with onboard EMG power extraction. This allows those using it to place it on the skin (of the subject 108) and wear it throughout the day. The wearable EMG sensor device 102 may be connected via Bluetooth to the mobile computing device 104 which enables the subject 108 to self-dose therapy regardless of location. Thus, therapy could be completed, for example, in a rehabilitation unit, a coffee shop, or a user's home. As the therapy is not restricted to a location, it allows users to perform therapy whenever and wherever is convenient for them.

The platform 100 may use the data transferred from the sensor device 102 to the mobile computing device 104 (or otherwise available to the mobile computing device 104 based on the data generated by the sensor device 102) to operate one or more games 112 that may be implemented by a mobile application executed by the mobile computing device 104. These games 112 can allow the user to practice control of both amplitude and timing of muscle contractions and relaxations, with adaptive strategies to keep the difficulty dependent on user progress. The sensor device 102 may periodically record EMG data throughout the day during gameplay and/or when the user is not engaged with the mobile computing device 104. In some embodiments, the data from logged from the performance and amount of game play, and the EMG and inertial activity when playing the games 112 may be synchronized to a device (e.g., server, computing device, storage device, etc.) of a cloud 114 for use by clinicians, therapists, and researchers to remotely monitor the use and performance of the user. Users of the platform 100 may include patients with spinal cord injuries (SCI) or other movement impairments, but is not limited to the foregoing.

Figure 2A:
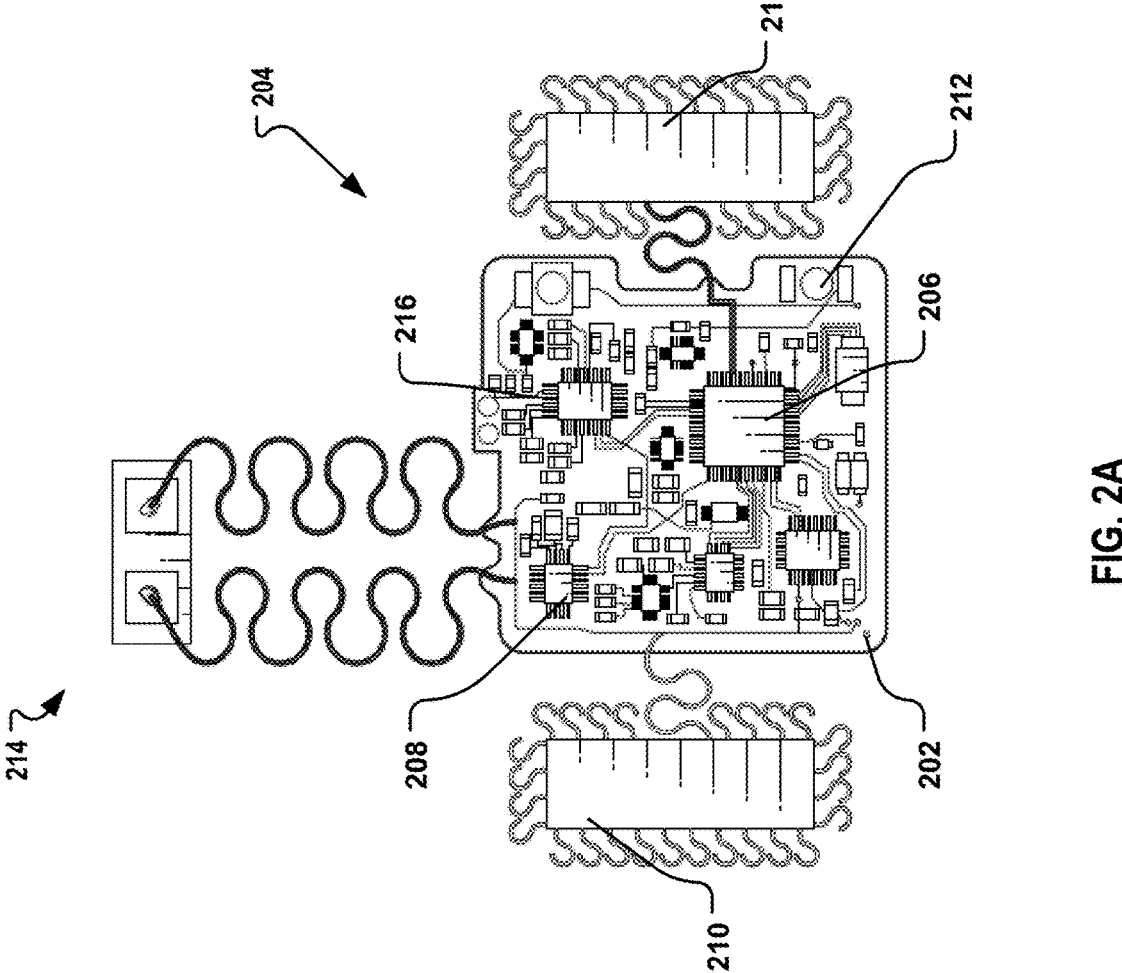
FIGS. 2A-2E are images of exemplary stages related to manufacturing a possible board layout associated with a wearable sensor device included within the platform of FIG. 1.
Figure 2A:
Figure 2B:
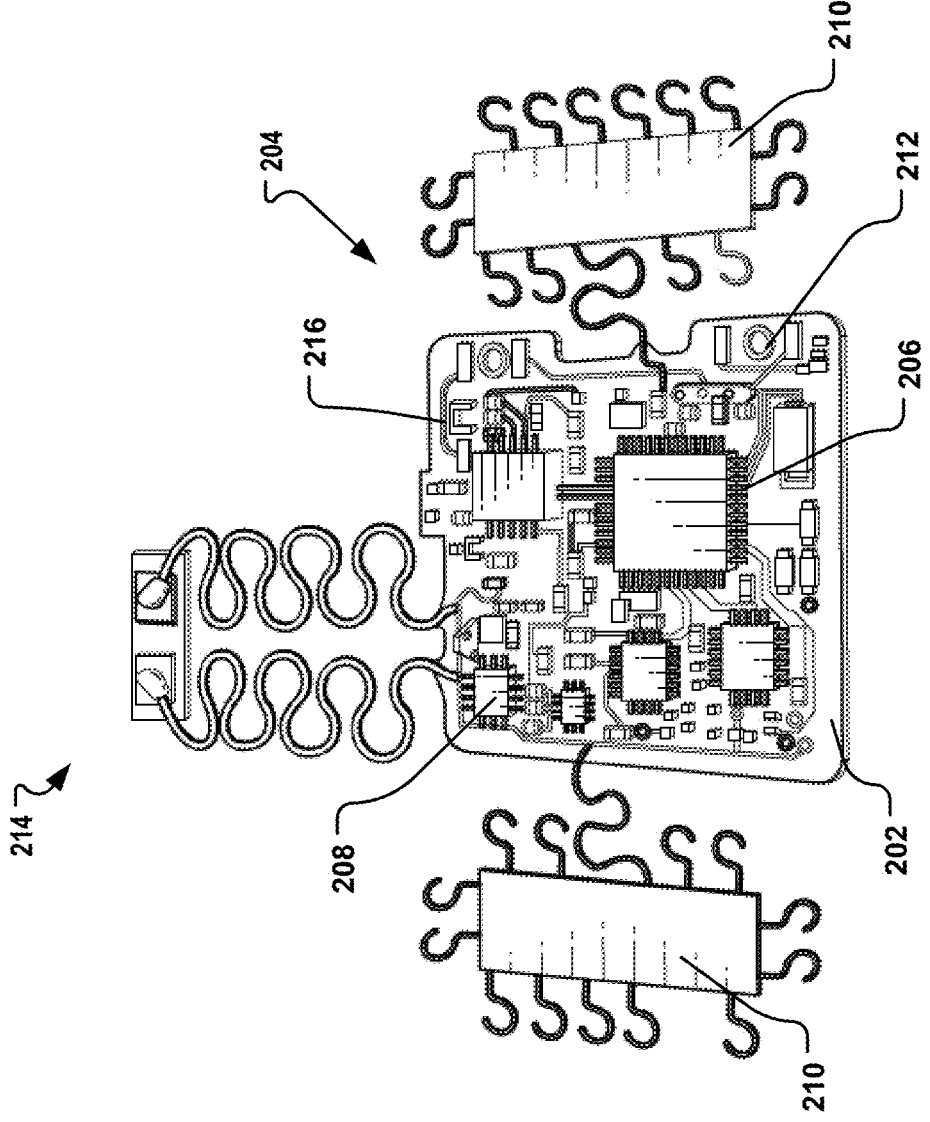
Figure 2C:
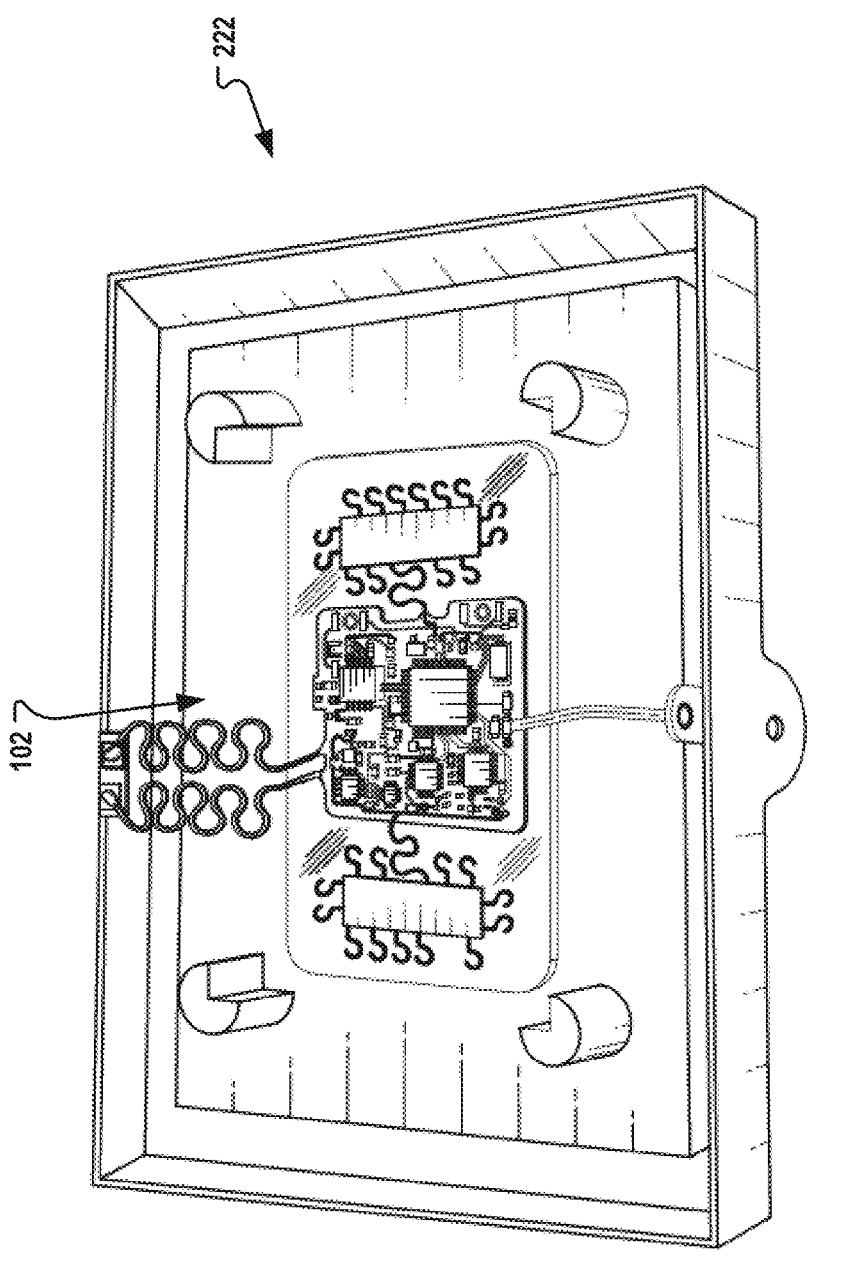
Figure 2D:
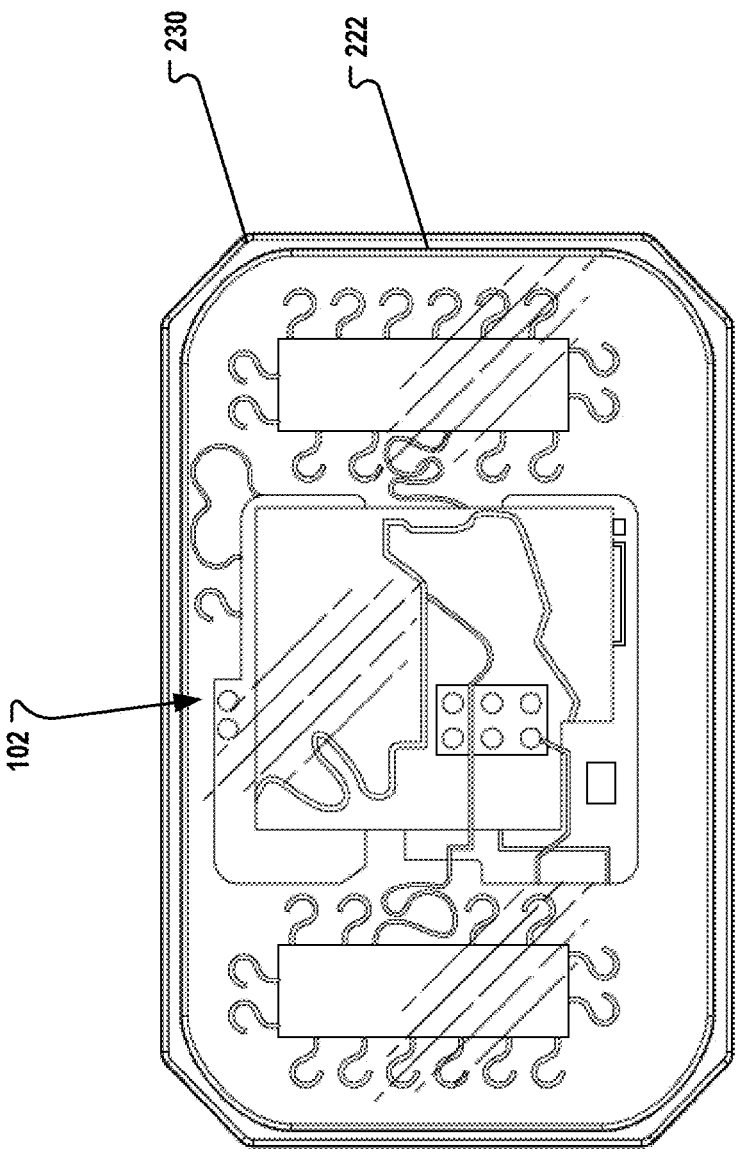
Figure 2E:
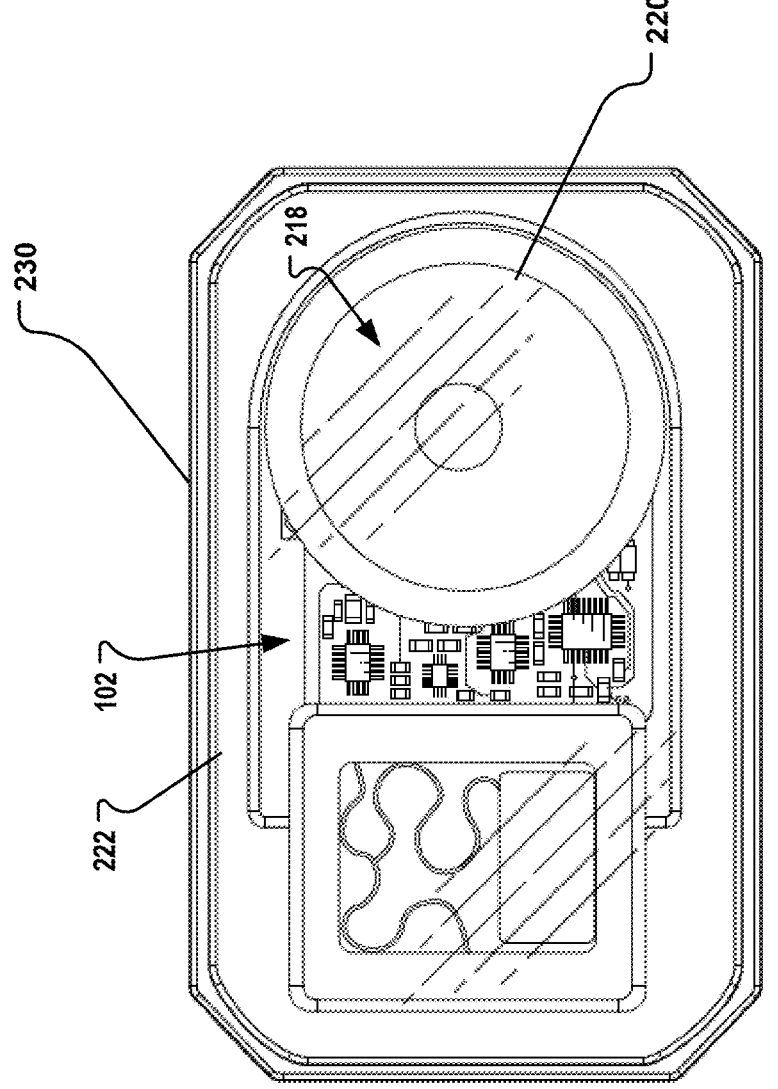

Referring to FIGS. 2A-2E, exemplary stages associated with assembly of the sensor device 102 is illustrated including possible components of the sensor device 102. In particular, FIG. 2A shows a substrate 202 in the non-limiting form of a printed circuit board (PCB) which may be flexible and generally provide supporting structure for a plurality of electrical components 204 of the sensor device 102. As indicated in FIGS. 2A-2B, the plurality of electrical components 204 may include a microprocessor 206, an inertial measurement unit (IMU) 208 (which may include one or more accelerometers, magnetometers, and gyroscopes), a plurality of electrodes 210, an antenna 212, a plurality of IMU sensors 214, and a plurality of conductive layers 216 or a bus interconnecting the plurality of electrical components 204. In some embodiments, the conductive layers 216 may include serpentine wires for enhanced flexibility and engagement to skin tissue. Referring to FIG. 2E, in some embodiments, the plurality of electrical components 204 further includes a battery 218 and a wireless charging station 220 electrically coupled with the substrate 202 and one or more of the plurality of electrical components 204, which may be configured for Qi wireless charging. In some embodiments, the contacts of the electrodes 210 shown in FIG. 2A may include gold, or silver/silver chloride.

In some embodiments, the substrate 202 is a 0.1 mm thick flexible PCB. As indicated in FIG. 2A, the electrodes 210 may be de-coupled from the substrate 202 yet electrically connected with serpentine wires making the sensor device 102 suitable and robust to twisting, stretching and rotation. They may then be embedded through a bottom layer of silicone with the rest of the circuitry floating above it. The EMG signals extracted by the sensor device 102 may be amplified and bandpass filtered before being digitized by the microprocessor 206 which may also manage Bluetooth connectivity. In some embodiments, firmware on the sensor device 102 digitizes the EMG data at 2 Khz and applies additional digital bandpass filtering. A waveform length algorithm may be used to extract EMG activity from subsequent 20 millisecond windows. Firmware of the sensor device 102 may expose this data under an EMG Bluetooth Service as both the raw digitized EMG and the EMG power via corresponding Bluetooth characteristics. The Bluetooth standard limits the frequency a characteristic can be updated, so multiple raw samples may be packaged into a single characteristic update to allow streaming the full 2 Khz bandwidth. A single EMG activity sample may be stored per characteristic to minimize the latency for real time feedback. The IMU 208 records the acceleration, rotation and magnetic data. This electrical component may be sampled at 500 Hz with the maximum rotation rate set to 500=s and maximum acceleration of 16 G. This inertial data may be captured or accessed by the microprocessor 206 used to generate a pose estimate (algorithm described below). An IMU Bluetooth service may organize this data which includes a characteristic for the accelerometer, gyroscope and magnetometer, respectively. Again, multiple samples may be bundled into each characteristic to facilitate streaming. A single pose estimate may be stored in a separate characteristic for every three raw data samples.

Accordingly, the sensor device 102 may generally take the form of a battery-powered, flexible, wearable EMG sensor device with wireless data communication capabilities. In use, the sensor device 102 may span across and record from a number of paretic muscles with any preserved activity, and/or multiple ones of the sensor device 102 may be implemented. When used in this therapy, the sensor device 102 may be placed directly onto the skin at a predetermined location suitable for recording electric signal activity. The sensor device 102 is capable of recording both EMG activity and inertial data (acceleration and rotation) and logging or streaming this data in real time over Bluetooth or other wireless technology.

As can be seen in FIG. 2C, the substrate 202 of the sensor device 102 may be disposed within a housing 222 and then (as seen in FIG. 2D, and FIG. 2E) the housing 222 may be entirely enclosed or encapsulated in an encapsulating layer 230, such as polydimethylsiloxane (PDMS), a silicone elastomer. The sensor device 102 is low-profile and wearable and has wireless charging via the wireless charging station 220 providing wireless charging through the Qi charging standard, Bluetooth connectivity, and also includes a 9-axis inertial measurement capability via the IMU 208. The sensor device 102 may also run firmware that provides logging functionality while the sensor device 102 is worn but not actively used for biofeedback as well as firmware to facilitate the EMG power extraction and streaming. When placed on the user, the sensor device 102 may periodically monitor and record the EMG power and inertial data to be downloaded later. When connected via Bluetooth, the sensor device 102 may allow continuous streaming of the EMG and inertial data. In some embodiments, the sensor device 102 can stream either the raw EMG data or after extracting the EMG power to allow balancing between bandwidth, power consumption and battery usage. When not streaming or recording to internal logs, the analog recording electronics power down to conserve battery usage. Data from the 9-axis inertial measurement unit 208 may be fused into an estimate of 3D orientation, and either the raw inertial measurement data or the orientation estimate can be streamed.

One embodiment of the aforementioned fusion approach may generally involve the simultaneous utilization of attitude and joint angle estimation via a custom quaternion-based complementary filter 250 and associated algorithm that runs on the sensor device 102. This algorithm is optimized to minimize distortions in the attitude estimate from biases in the magnetometer of the IMU 208. The efficient quaternion-based attitude estimation algorithm may be designed that it can be implemented in real-time on the wearable sensor device 102.

Figure 2F:
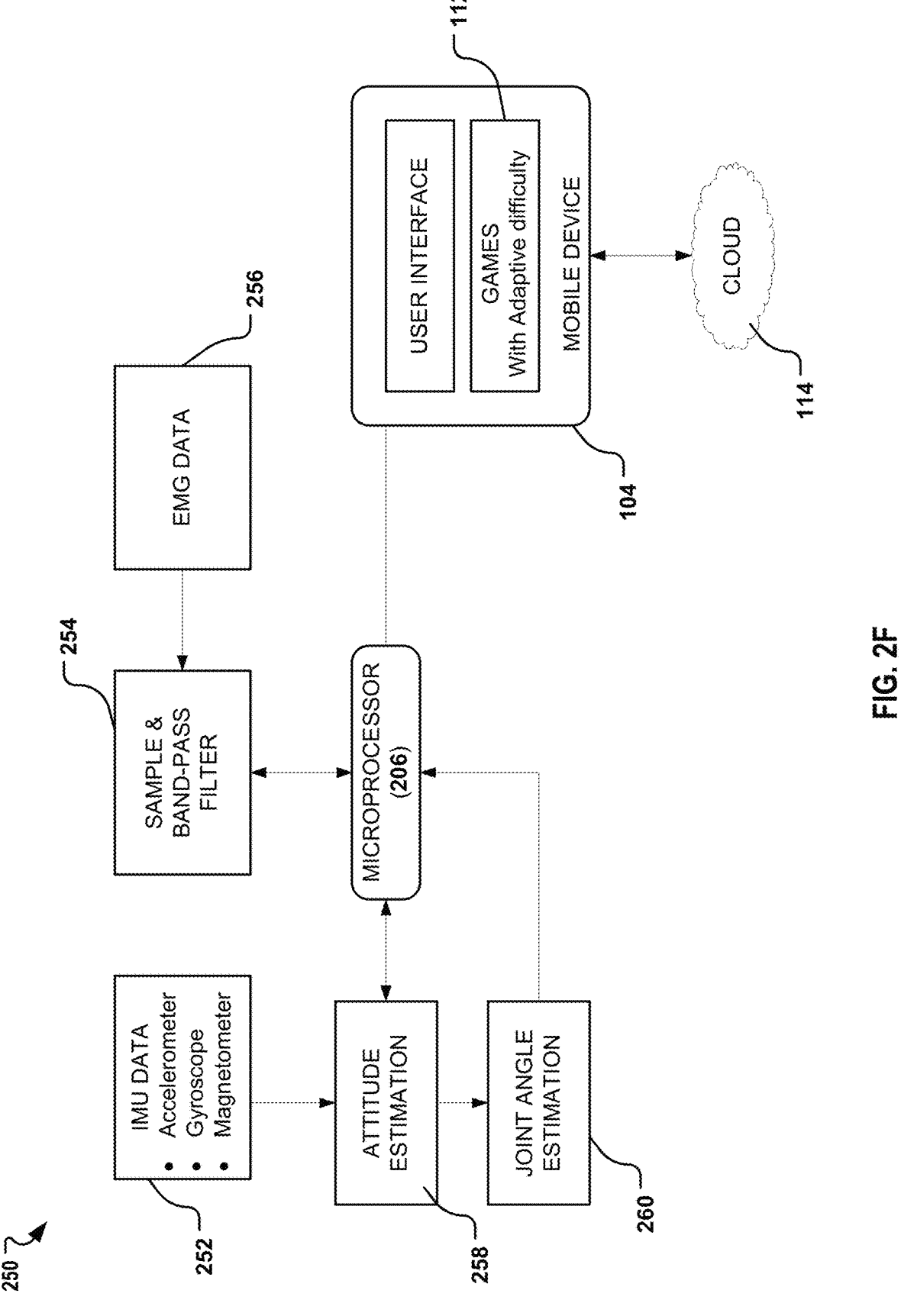
FIG. 2F is a simplified block diagram illustrating data processing including filtering of signal data handled by the sensor device 102 and exchange of the filtered data with the mobile device.

FIG. 2F illustrates aspects of the quaternion-based complementary filter (hereinafter "filter") 250 and associated algorithm further described below, which may be executed via the microprocessor 206 of the sensor device 102. As indicated, the filter 250 may generally leverage IMU data 252 extracted by the IMU 208 from at least one accelerometer, gyroscope, and magnetometer of the IMU 208. The filter 250 may further utilize a sample & bandpass filter 254, and EMG data 256 from the electrodes 210 of the sensor device 102. In general, the microprocessor utilizes the IMG data 252 and the EMG data 256 to compute attitude estimation 258 and joint angle estimation 260.

By way of some introduction, quaternion math relates to a four element vector representation of orientation with unit length that be easily converted back into Euler angles (roll, pitch and yaw). They have the benefit of being compact, efficient to work with, and not suffering from gimbal lock. Complementary filters may be used to compute pose estimate from 9-axis inertial data. They work by integrating the gyroscope measurements (of the IMU 208) to obtain a good high frequency response and use the accelerometer and magnetometer for improved slow frequency response by correcting for gyroscope drift. The quaternion-based complementary filter may be used by the sensor device 102 to provide more robust attitude estimates across the variety of poses a person may take. The axis convention for this filter uses the NED (North-East-Down) convention common in aeronautical systems. Measurements will be described as either in the world reference frame of the sensor reference frame.

Let $\omega$ be the vector of rotation rates (in rad/s) along each axis, measured by the gyroscope, and q be the quaternion representation of the current pose. The gyroscopes also have a bias ($\omega_b$) that changes over time and it is contemplated that the filter track this too. If the gyroscopes measurements and bias were perfect, the state could be propagated forward in time from these measurements using the matrix that transforms from angular rates to a change in the quaternion state and then integrating this dynamical system.

$$\Omega(q) = \begin{bmatrix} -q1 & -q2 & -q3 \\ q0 & -q3 & q2 \\ q3 & q0 & -q1 \\ -q2 & q1 & q0 \end{bmatrix} \tag{1}$$

$$\dot{q} = \frac{1}{2}\Omega(q)(\omega - \omega_b)$$

However, inevitable errors in the gyroscope measurements and changes in bias will be accumulated, resulting in a drift in the attitude estimate. This drift can be corrected with the accelerometer and magnetometer readings, which provide a reference to the world frame.

In a stationary frame the accelerometer should only measure gravity, which is a good first approximation for participants not moving significantly. Thus any misalignment between the accelerometer axis and the predicted gravity (down) axis is an error. The rotation to correct that error can be computed by taking the cross product between the measured and predicted acceleration. To compute the predicted acceleration $R_{be}$ is is used which rotates a vector from the world frame into the sensor (body) frame. Let a be acceleration measured along each axis in the sensor reference frame and g point in the upward direction.

$$R_0 = [\, q_0^2 + q_1^2 - q_2^2 - q_3^2 \quad 2(q_1q_2 + q_0q_3) \quad 2(q_1q_3 - q_0q_2) \,]$$

$$R_1 = [\, 2(q_1q_2 - q_0q_3) \quad q_0^2 - q_1^2 + q_2^2 - q_3^2 \quad 2(q_2q_3 + q_0q_1) \,]$$

$$R_2 = [\, 2(q_1q_3 + q_0q_2) \quad 2(q_2q_3 - q_0q_1) \quad q_0^2 - q_1^2 - q_2^2 + q_3^2 \,]$$

$$R_{be}(q) = [\, R_0^\top \quad R_1^\top \quad R2^{\top} \,]^T \tag{2}$$

$$e = \frac{a}{\|a\|} \times R_{be}g \tag{3}$$

The accelerometer correction does not give any feedback to the heading estimate, but heading can be disambiguated with the magnetometer. However, magnetometers are more susceptible to distortions than gravity so it is desired to constrain this update to only influence heading $\psi$. This is done by projecting the analogous correction from the magnetometer onto the derivative of the quaternion state with respect to a change in heading, $$\frac{\delta_q}{\delta_\psi}.$$

It is also important to compute the predicted magnetic flux ($B_e$) for a given location using the world magnetic model. Let m be a vector containing the magnetic flux measured along each axis.

$$e_m = \frac{m}{\|m\|} \times R_{be}B_e$$

$$\frac{\delta q}{\delta\psi} = [\, -q_3 \quad -q_2 \quad q_1 \quad q_0 \,]^\top$$

-continued $$\dot{q}_m = \left(\frac{\delta q}{\delta \psi} \cdot \frac{1}{2}\Omega(q)e_m\right)\frac{\delta q}{\delta \psi}$$

The updates from the gyroscope, accelerometer, and magnetometer can then be combined to create a robust pose estimate:

$$\dot{q}=\frac{1}{2}\Omega(\dot{q})(\omega=\omega_b+K_{pa}e_a)+K_{pm}\dot{q}_m \qquad (4)$$

$$\dot{q}_{t+1}=a_t+\dot{q}\Delta_t \qquad (5)$$

It is also helpful to track changes in the gyroscope bias as this can change with time and temperature. Both $e_a$ and $e_m$ are the rotational errors in the body frame which makes them easy to feed back. However, again it is important to constrain the magnetometer changes to only the heading axis (which depending on the sensor orientation can map to any axis in the sensor frame). This can be done using the transpose of $\Omega(q)$.

$$\omega_{b,t+1}=\omega_{bt}-K_{ia}e_a-K_{im}\Omega(q)^T\dot{q}_m \qquad (6)$$

Figure 3:
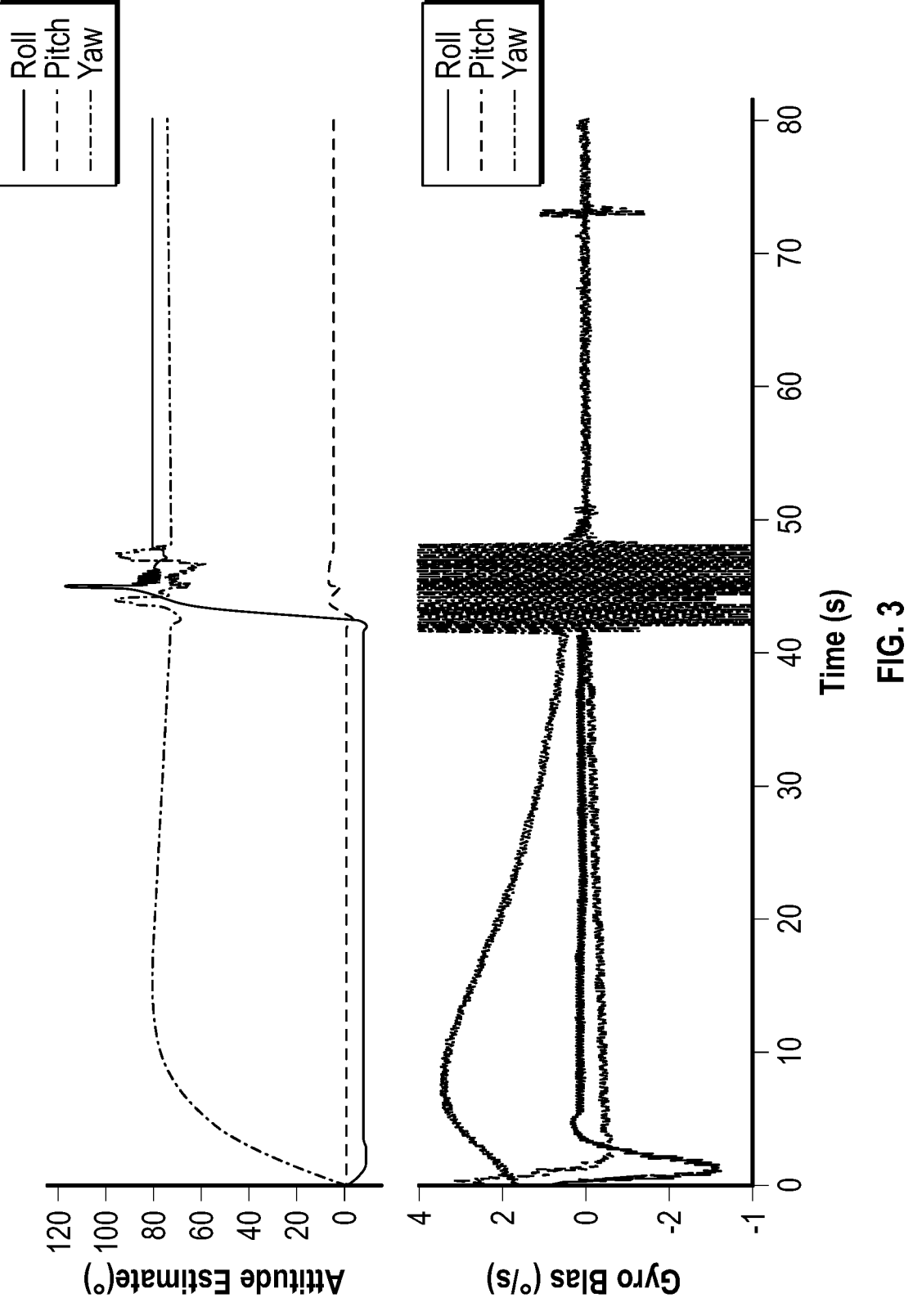
FIG. 3 is a plurality of graphs illustrating gyro bias tracking and attitude convergence from a poor initialization. A sensor was enabled and left flat for 40 seconds and then rotated to vertical. The top panel shows the online attitude estimate converging to the correct values then stabilizing. The bottom panel shows the gyroscope measurements after bias correction demonstrating them being corrected to zero bias. For the initial segment when the sensor is flat only the magnetometer measurements influence the yaw bias, hence the different time scale.

This pose filter (attitude estimation 258) may be implemented in C to run on the microprocessor 206. Having an online implementation is useful when using Bluetooth as otherwise gaps or dropped data can make offline reconstruction challenging. FIG. 3 shows the pose estimate and gyro calibration in two positions, with the attitude holding steady in each after convergence. The bias corrected gyro measurements correctly tracks to zero, showing a slightly different time course for different axes due to a differing values of $K_{ia}$ and $K_{im}$.

In some embodiments, each sensor device 102 produces a quaternion pose estimate and visualizing these directly is not an intuitive way to understand their relative orientations. Luckily, calculating the relative rotation between two quaternions is fairly straightforward. The quaternion inverse $q^{-1}$ is an operator that reverses a rotation. If the poses from two sensors are r and s, then $q=r^{-1}s$ is the 3-dimensional rotation from the former to the latter. This can be further decomposed into the rotational angle ($\theta$) and the axis (v) of that rotation.

$$\theta(q) = \arctan\left(\sqrt{q_1^2 + q_2^2 + q_2^2}, |q_0|\right) \qquad (7)$$

$$v(q) = \frac{1}{\sqrt{1-q_0^2}}\begin{bmatrix}q_1\\q_2\\q_3\end{bmatrix} \qquad (8)$$

While this is mathematically correct, in practice it will not give the desired angle. This is because the sensors can be positioned on the limbs arbitrarily and this rotation must be accounted for. This can be resolved by measuring the pose of each sensor with the joint at neutral and removing this baseline orientation from subsequent measurement, thus in effect mathematically aligning the two sensors in this position. Next, the angle between these corrected orientations ($\hat{r}$ and $\hat{s}$) is estimated with Eq. 7.

$$\hat{r}_t = r_0^{-1}r_t \quad \hat{s}_t = s_0^{-1}s_t \qquad (9)$$

$$\theta_{r \to s} = \theta\left(\hat{r}_t^{-1}\hat{s}_t\right)$$

Figure 4:
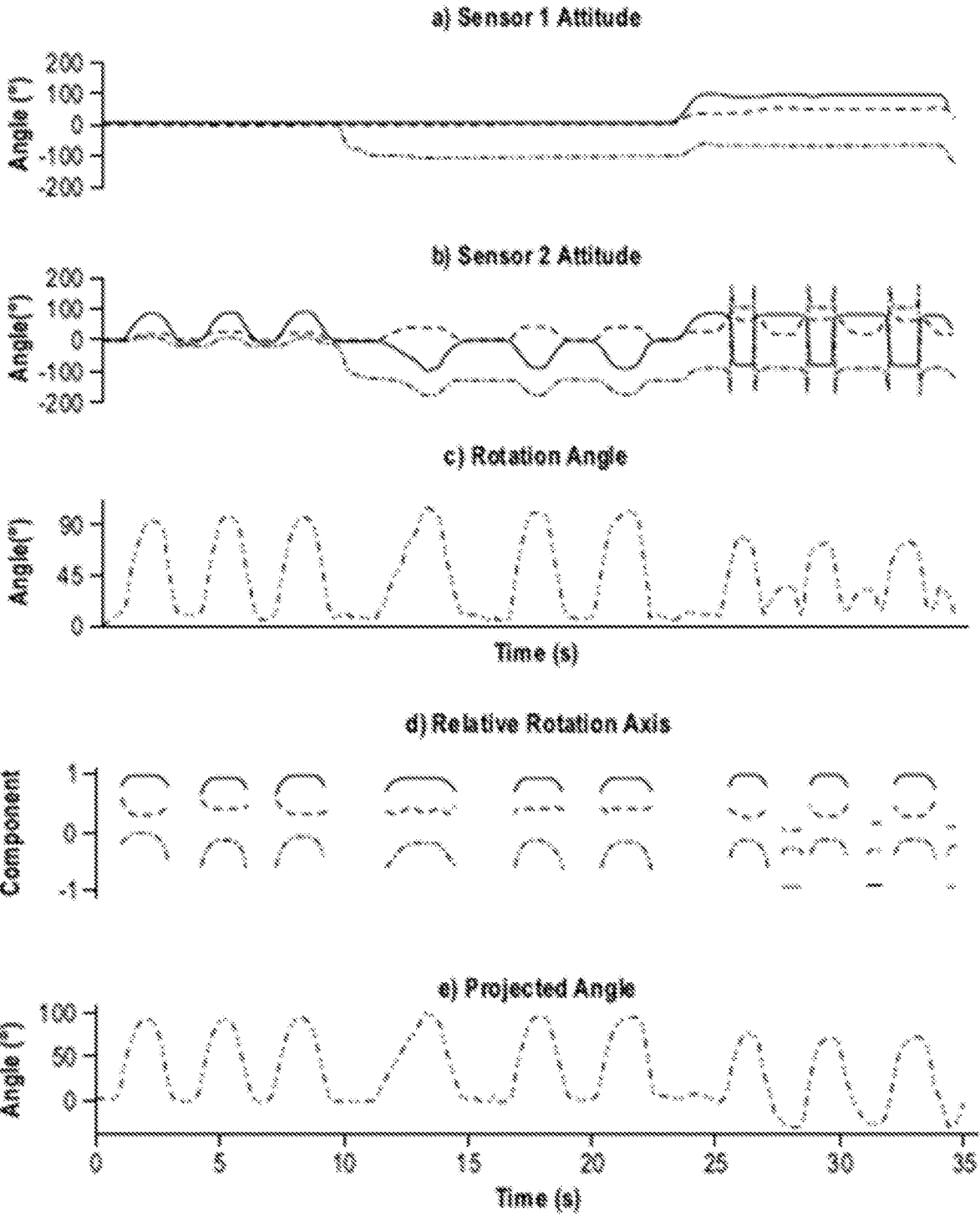
FIG. 4 is a plurality of graphs relating to two sensors mounted across a rigid hinge rotating around three different directions: a) and b) the absolute orientation of the two sensors, c) rotation magnitude between two attitudes, d) axis of rotation, relative to the first sensor, and e) rotation angle projected along dominant rotation axis.

FIG. 4 demonstrates this algorithm with two sensors mounted on a rigid hinge. Sensor 2 was rotated ninety degrees relative to sensor 1 multiple times, and then the orientation of the entire hinge was changed. As desired, the estimated rotation angle continues to capture the real angle. The axis of rotation between the two sensors can be measured with (Eq. 8) and is shown in FIG. 4, showing this is constant despite the whole system rotating, which a hinge physically enforces.

This constant axis constraint of a hinge joint is true for many joints in the body, although of course the shoulder and hips are multi-axial and even the elbow admits some supination and pronation. It can be exploited by estimating this axis relative to one of the sensors and then estimating the joint angle as rotation only around this axis. This can be done easily with a different representation of orientation called a rotation vector (Eq. 10), which uses a three element representation that folds the unit norm of a quaternion into it. This has the benefit of keeping many properties of rotation Cartesian. Because of this principal component analysis may be leveraged to project the rotation vector only along the first principal component, v, which also represents the axis of rotation as a unit norm vector. The rotation angle around v is the length of this projection (in radians).

$$r = [\,q_1 \quad q_2 \quad q_3\,]^T \frac{1}{\sqrt{1-q_0}} \qquad (10)$$

$$\theta = r \cdot v \qquad (11)$$

The benefits of this additional step for data visualization can be seen in the last panel of FIG. 4 ("4e"). In the last three movements when the hinge was oriented vertically it was extended past the zero reference. In this case the angle estimated with Eq. 9 shows a unique characteristic since it does not preserve the sign but Eq. 11 does. This step also makes the analysis slightly less sensitive to calibrating the zero pose. If rotation around two axes is desired, such as to measure supination at the elbow, more sophisticated methods can be used.

Finally with the joint axis identified, rotation rate around this axis can be measured directly by transforming the gyroscope measurements. The difference between these transformed rotations between each sensor should be the same as the derivative of the estimated joint angle estimated above. This provides a check for consistency check, and also can be more accurate for the higher frequency structure such as if the rotational velocity is explicitly desired. This is performed with the same inverse rotation that generated the neutral pose above applied to the gyroscope measurements, and then projecting the rotated rotation rates along v.

In one embodiment, the specifications of the sensor device 102 software may be as follows:

100× analog gain with 15-300 Hz bandwidth. SAADC sampling at 2 khz with 16× oversampling;

Digital 5th order FIR with 40-120 Hz BW followed by EMG power extraction using window length algorithm;

Custom Bluetooth endpoints allow fine selection of which EMG or inertial activity requested;

Highly power optimized with 150-200 µA consumption while logging and 2 mA while streaming; and Attitude estimation from 9-axis IMU using optimized complementary filter.

However, it should be understood that the present application is not limited to the above sensor software configuration. Other software may be implemented with the sensor device 102 provided it is capable of meeting the requirements of the platform 100 of the present application.

Figure 5A:
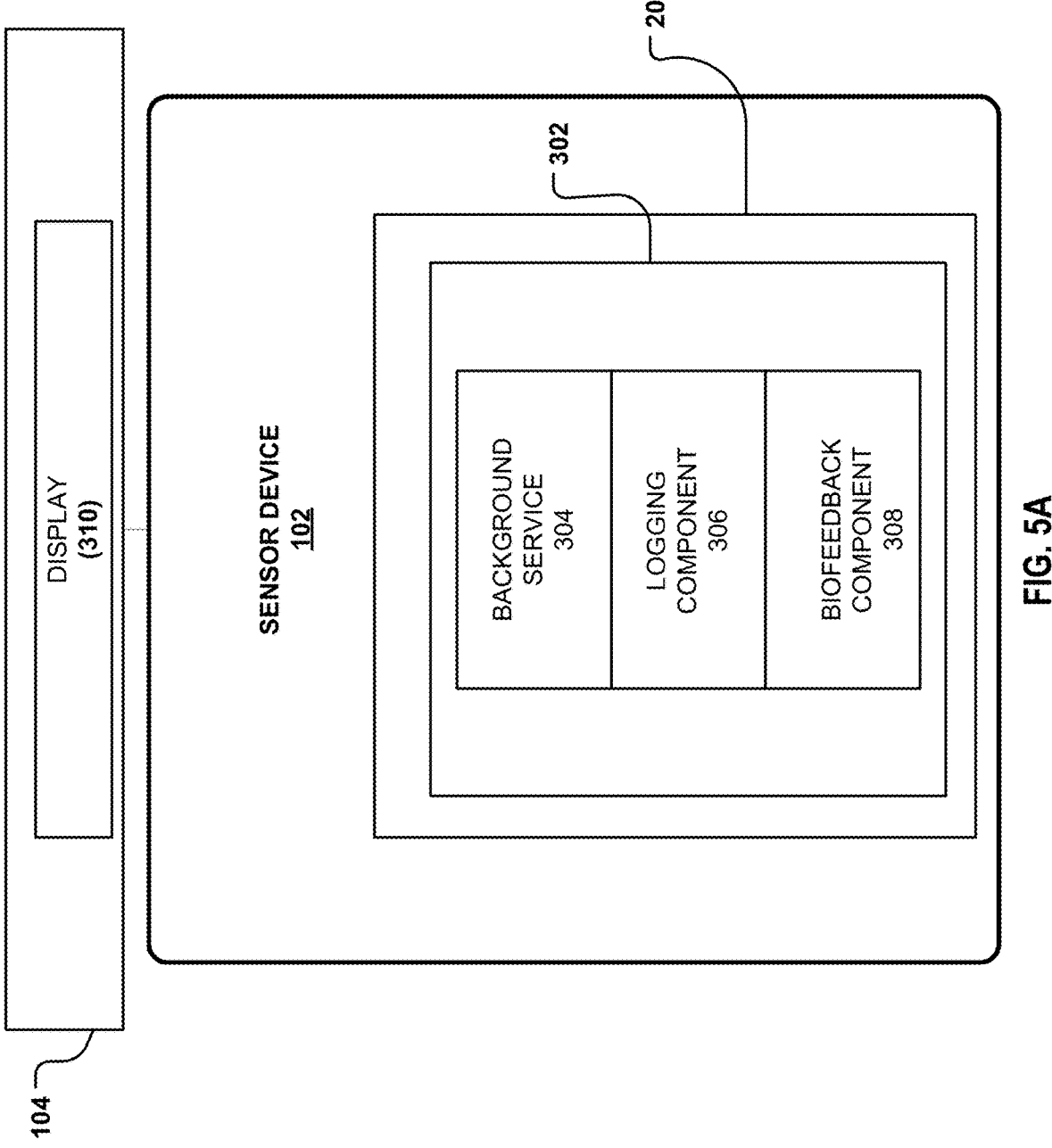
FIG. 5A is a simplified block diagram of a software stack for an application or firmware which may be utilized with the platform of FIG. 1.
Figure 5B:
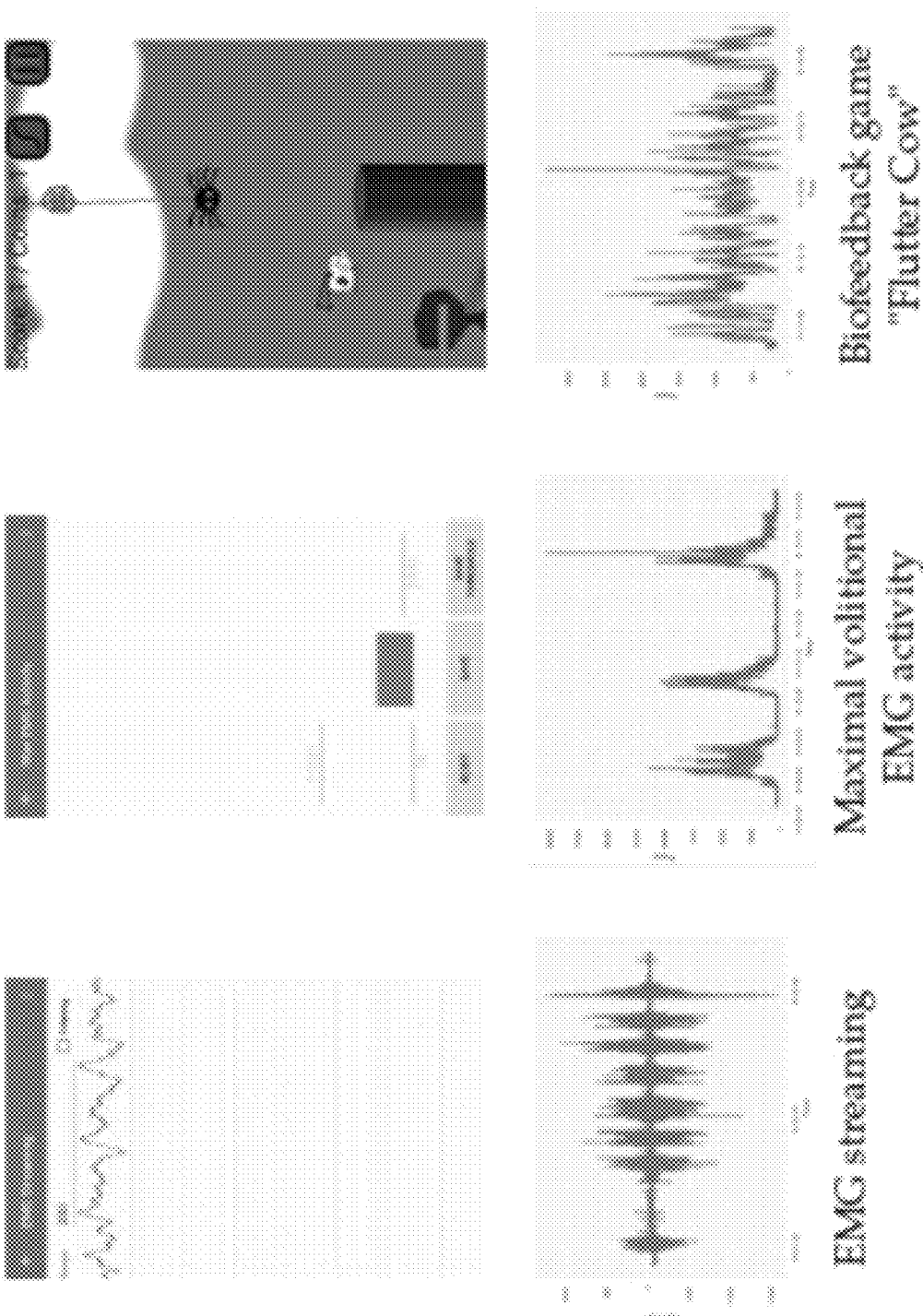
FIG. 5B is an illustration of exemplary display images of electromyographic feedback associated with an application executed by a computing device of the platform of FIG. 1.

Referring to FIG. 5A, one embodiment of an application 302 or firmware is shown, aspects of which may be executed by the microprocessor 206 of the sensor device 102. The application 302 may define or otherwise include a background service 304, a logging component 306, and a biofeedback component 308. The background service 304 manages connectivity to the mobile computing device 104 for the logging and biofeedback components and uploading that data to the cloud 114 or other storage environment. The logging component 306 can periodically download logs of EMG and inertial activity from the sensor device 102 to the mobile computing device 104 that may be connected to the sensor device 102 via Bluetooth or other wireless method. The biofeedback component 308 can provide information leveraged by a plurality of games executable by the mobile computing device 104 and rendered along a display 310 of the mobile computing device 104. In other words, the biofeedback component 308 exchanges data with a suite of games or other applications that can be controlled by or otherwise react to data streamed between the wearable sensor device 102 and the mobile computing device 104.

Figure 6A:
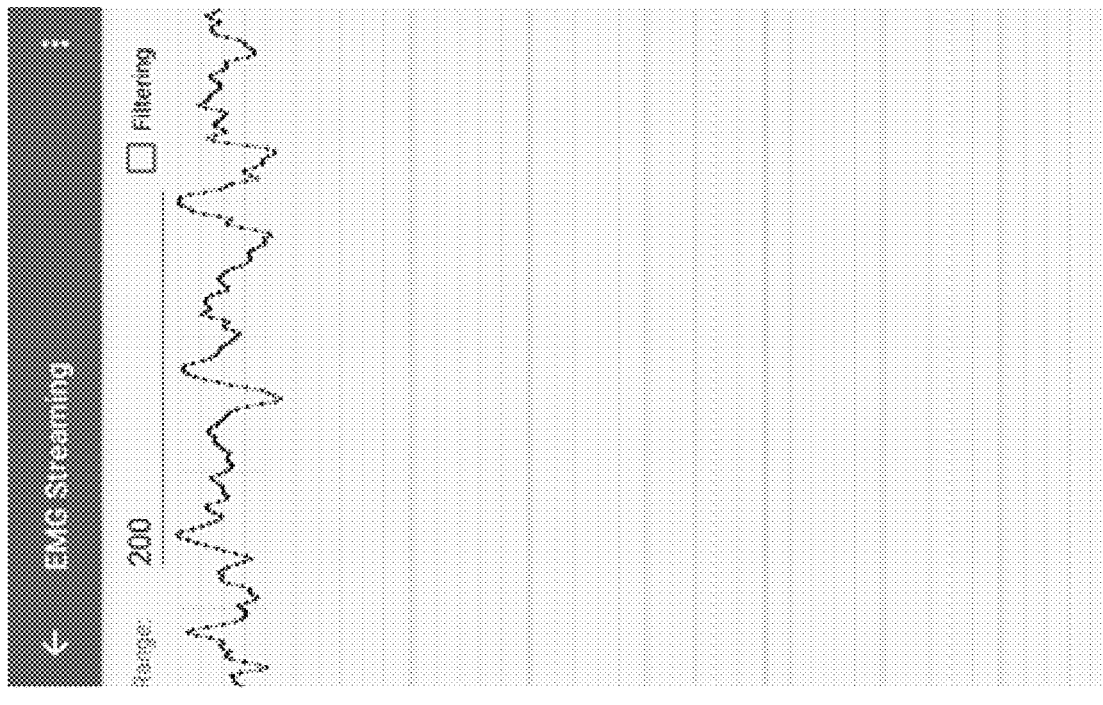
FIG. 6A is a detailed view of EMG streaming displayed by any computing device associated with the platform of FIG. 1 leveraging electromyographic feedback generated by a wearable sensor device.
Figure 6B:
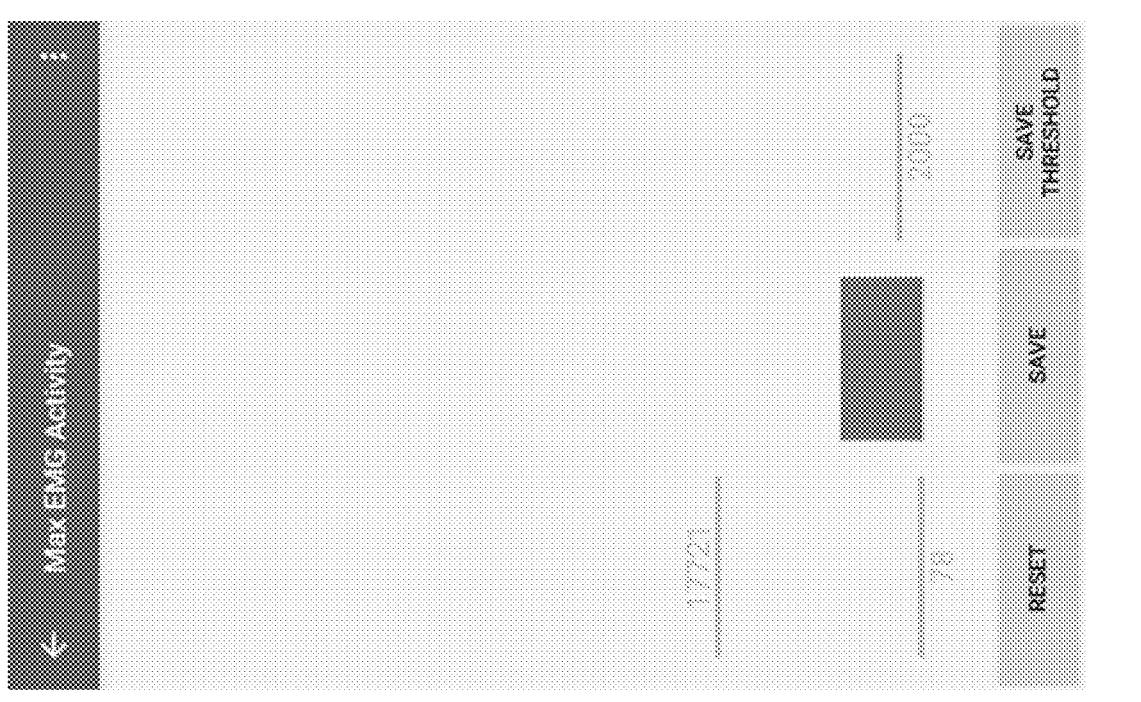
FIG. 6B is a detailed view of maximum EMG activity displayed by any computing device associated with the platform of FIG. 1 leveraging electromyographic feedback generated by a wearable sensor device.
Figure 6C:
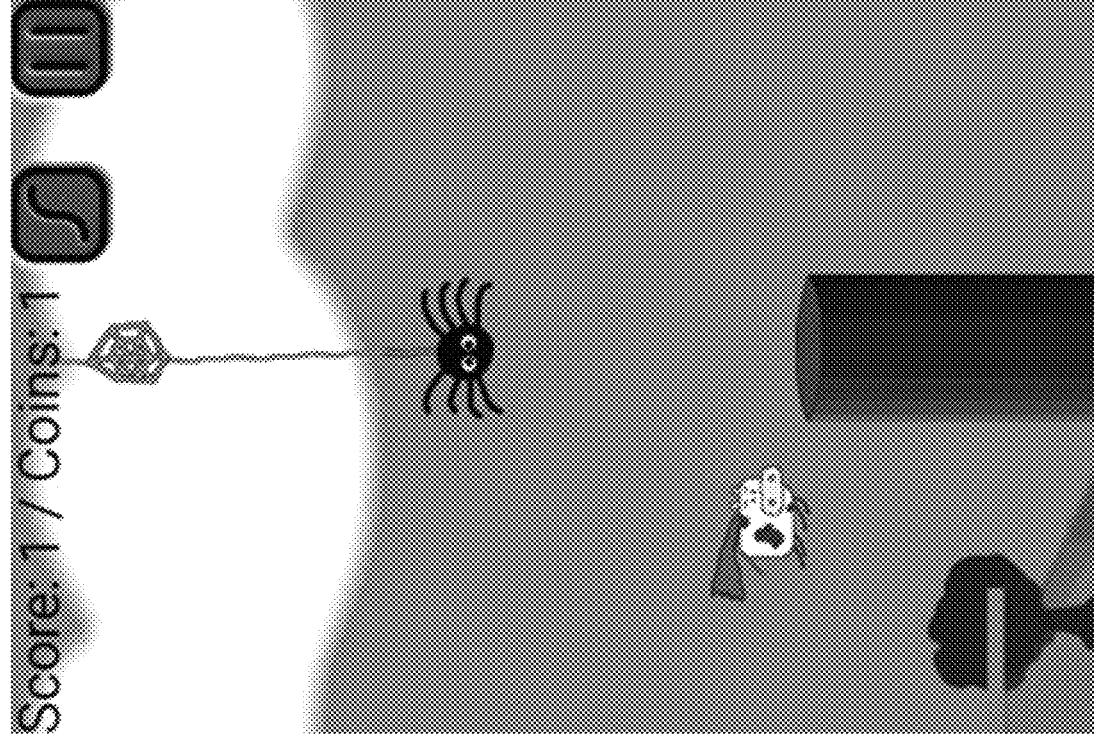
FIG. 6C is an exemplary display image of a game executable by any computing device such as a mobile computing device associated with the platform of FIG. 1 that provides electromyographic feedback in cooperation with a wearable sensor device.
Figure 6D:
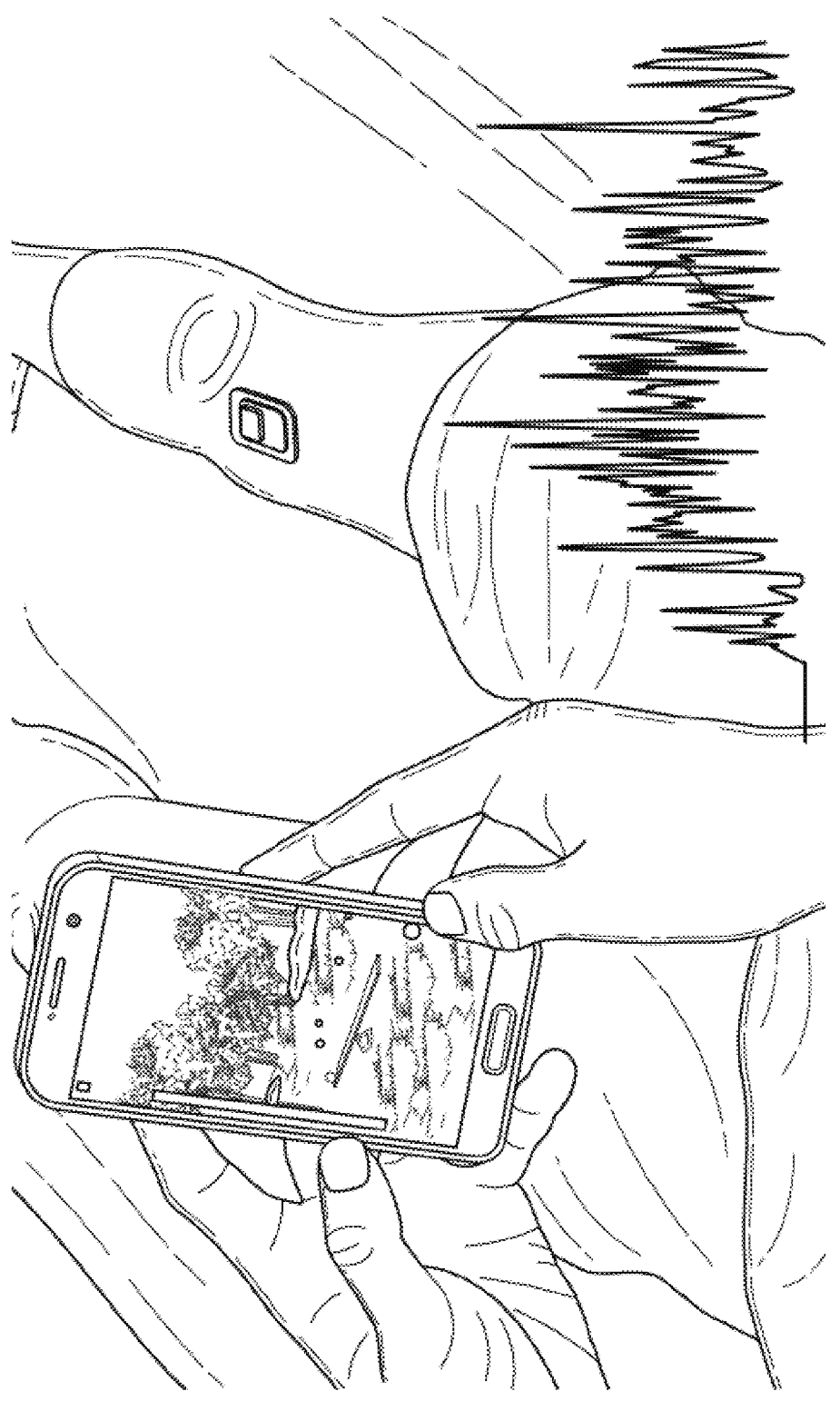
FIG. 6D is an image of a user interacting with a possible biofeedback game which generates biofeedback information from the sensor device for biofeedback therapy.
Figure 6E:
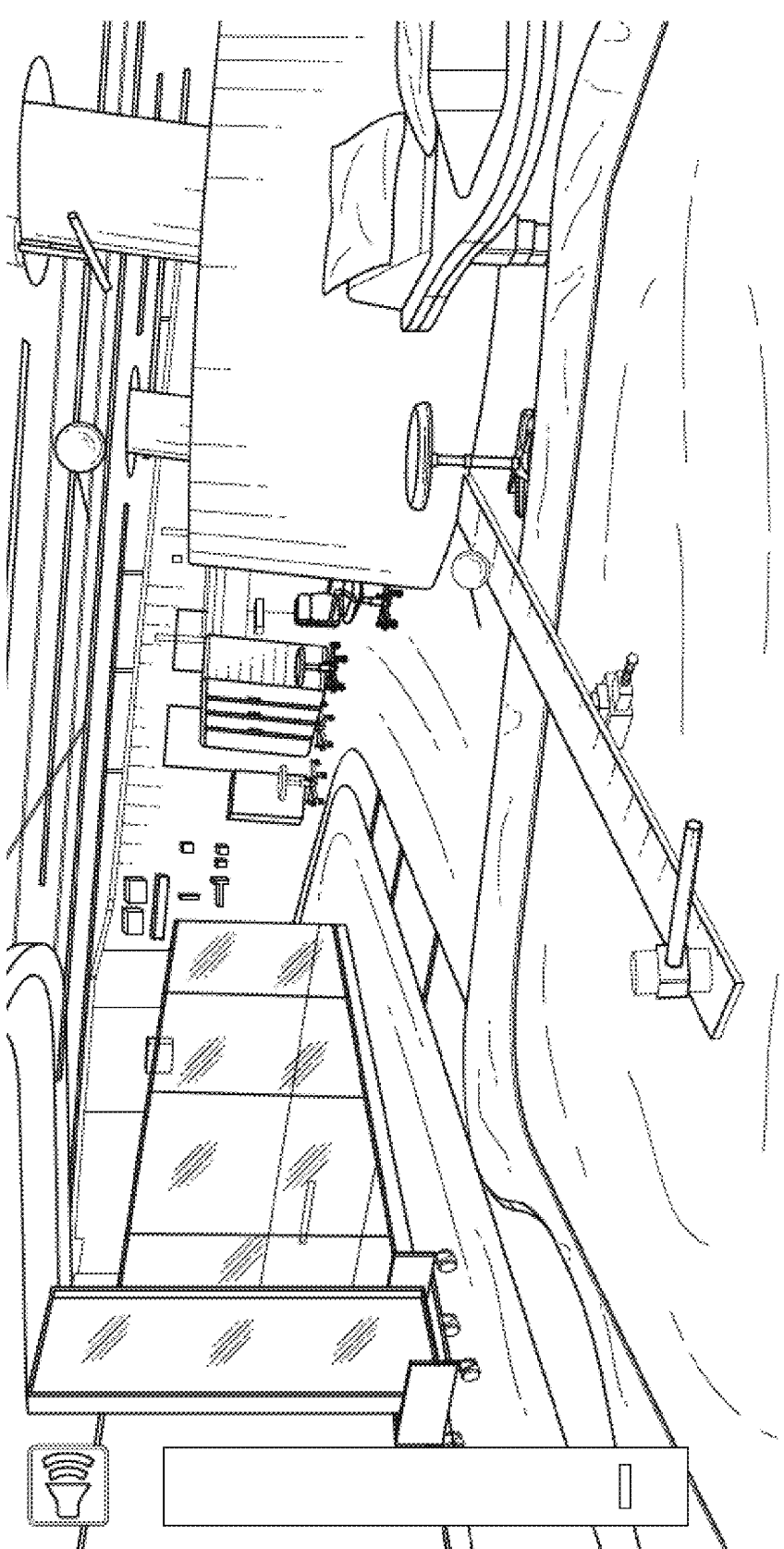
FIG. 6E illustrates further detail regarding the possible biofeedback game of FIG. 6D.

Referring to FIG. 5B and FIGS. 6A-6E, a plurality of images are shown; each of which may be rendered along the display 310 of the mobile computing device 104 to a user, and/or displayed or presented via any additional computing device to the user/subject, or to other possible users such as clinicians or administrators. FIG. 6A, for example, shows exemplary detail regarding EMG streaming as interpreted by the sensor device 102 which may be displayed along the display 310 or otherwise rendered as desired. FIG. 6B shows exemplary detail of maximum EM activity as interpreted by the sensor device 102 which may be displayed along the display 310 or otherwise rendered as desired. FIG. 6C shows exemplary detail regarding a possible game which may be executed by the processor 301 and may be part of the application 302 or separately accessed and executed by the processor 301. When engaging a game as depicted in FIG. 6C, the sensor device 102 may generate biofeedback information during gameplay, which may affect the game, and be useful for therapy and analysis thereof. Other embodiments of games are shown in FIGS. 6D-6E and described herein.

Figure 6F:
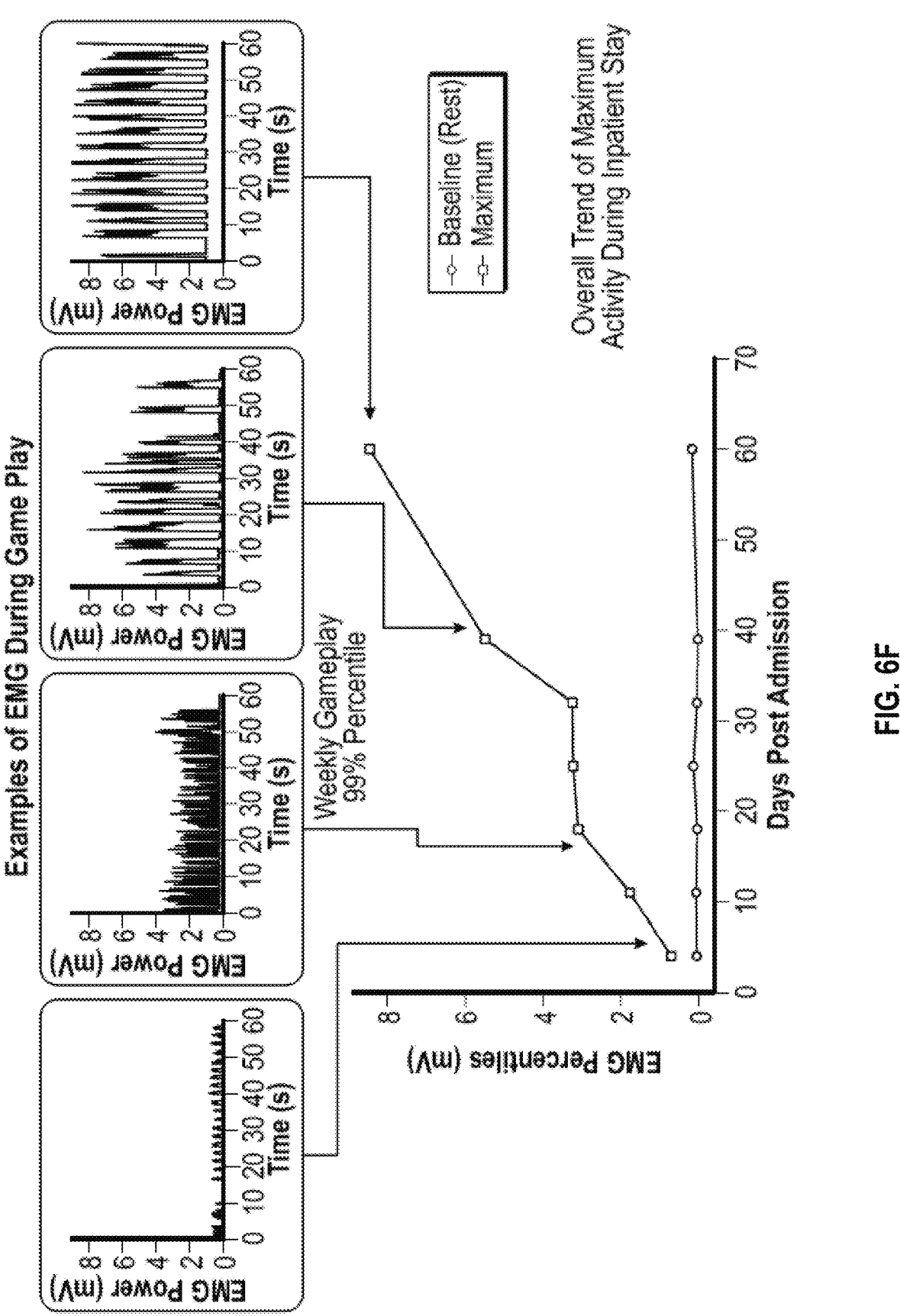
FIG. 6F illustrates examples of EMG activity generated by the platform during gameplay by a user.
Figure 7:
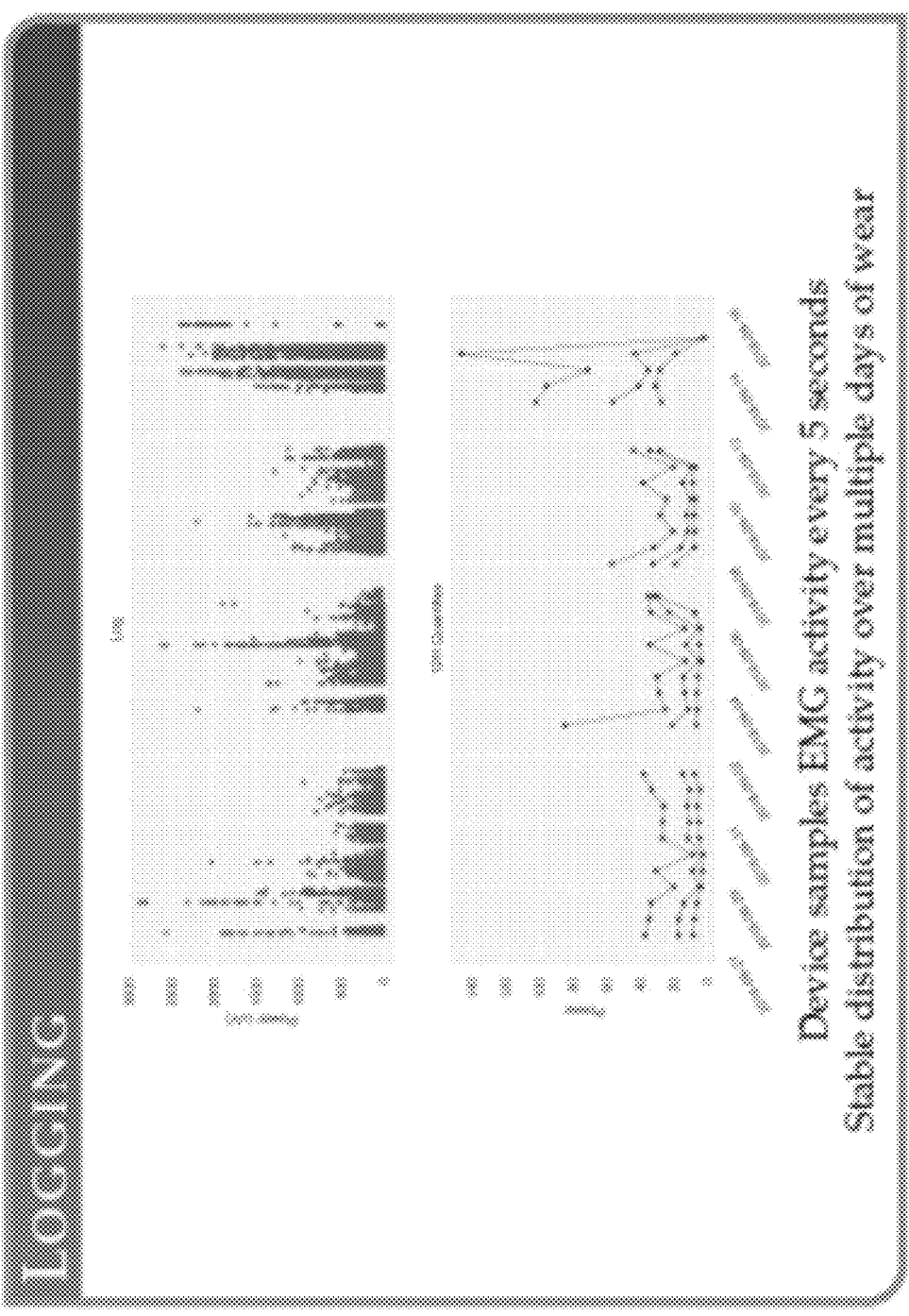
FIG. 7 is an exemplary log of EMG activity generated by the platform of FIG. 1.

Biofeedback games executed by the mobile computing device 104 may be designed to encourage users to repeat certain behaviors that are thought to help recovery or provide some self-dosed therapy. These games are controlled by either EMG or inertial activity, which can be streamed from the wearable sensor device to the device in real time. The games can be controlled by the user manipulating their muscle activity (activating or relaxing the muscle) or moving their limbs to manipulate the game. Information regarding game play as well as EMG and inertial activity during game play can then also be uploaded to the cloud server for review by clinicians, researchers, and therapists to also monitor the user's results and guide therapies. This can be analyzed either in real-time or retrospectively. Measures of changing muscle activation can be extracted from gameplay. An example of improving muscle activation as measured from biofeedback games from a user with spinal cord injury over 60 days is shown in FIG. 6F. Exemplary logs of EMG activity are depicted in FIG. 7.

Biofeedback games executed by the mobile computing device 104 or otherwise engaged by the user may be designed to be enjoyable in to make it more pleasant for users to engage in more self-dose biofeedback therapy and increase the amount of therapy. Some of these design decisions include but are not limited to making the games easy to play for short intervals that are available ("casual gaming"), giving the user visual and auditory rewards for engagement and performance, presenting graphs or other visual feedback of time spent engaging in self-dosed biofeedback and their performance, and using augmented or virtual reality. Users may set goals of daily biofeedback and see a log if they achieved this. Prompts may be displayed on the phone to remind a user to engage in biofeedback games when they are below their goal.

The difficulty of the games, based on how much muscle activation is required to play, also adapts based on the user's current abilities. For users with weaker muscles (less volitional EMG activity) it will require less activation to have the same result in the game. As muscle activity increases with time, the difficultly will increase. This adaption is to keep the games challenging but also playable. This adaptive difficulty will also encourage users to try harder while self-dosing therapy as they recover more strength.

The software of the games may be programed in order to encourage participation from users that have minimal volitional EMG activity. EMG activity may be recorded from each user at the start of the program. The difficulty of the game can then be adjusted based on the detectable level of EMG activity. This can be important to encourage the training of those with less EMG activity in order to mitigate the possible frustration that constantly losing at the game could cause. As the game difficulty is user dependent, the games become more difficult as the user becomes more able to control his/her muscles.

To facilitate this changing interface, EMG signals may be collected through the wearable sensor device 102 and sent via Bluetooth to the game. The game will then have appropriate programming to determine the level of game play available to the user based on the placement of the EMG signals on a scale. Those on the bottom of the scale (weaker EMG signals) would be shown easier challenges to correspond with their ability while those at the top of the scale (stronger EMG scales) would be shown harder challenges within the game. The learning algorithm behind the games would be programed to evaluate the input of the EMG signals and the appropriate gameplay to provide for each user.

In one example of a game shown in FIG. 6C, there is a pillar displayed on the bottom of the screen and directly above it there is a spider hanging from the top of the screen, with empty space between the two. The player's objective is to move a character through the empty space by moving the character up or down as it moves at a constant speed forward. The biofeedback in this game is present when the user contracts her muscle to move the character up. As the user relaxes her muscle, the character falls down. Alternatively, the character may go up when the user completes a cycle of contraction and relaxation and then begin to fall again. For patients with weaker EMG signals, the sensor would relay the weak signal to the game which would in turn recognize weaker EMG signals to move the character. Furthermore, the weaker EMG signals would instruct the game to adjust to respond to the user's needs. For instance, the game could display more space between the pillar and the spider, allowing the user more leniency in passing the levels and getting more points. As the user's EMG signal gets stronger, the game reacts in the opposite way. For instance, stronger EMG signals may be required to successfully move the character up or down. Alternately, the pillar and spider may be positioned closer together or more pillar and spider combinations could be placed closer together.

This makes it harder for the stronger signaled EMG users to score as many points and to better control their muscle movements by watching the biofeedback on the screen in the form of the character navigating the obstacles.

Another exemplar EMG biofeedback game to help users increase their volitional muscle activation is shown in FIG. 6D. In this game the user must activate their muscle that is being recorded by the sensor as much as they can for several seconds when cued. With greater activation, the hammer is brought back further and then comes down more forcibly. This launches a ball in the air that goes further for greater activation. With sufficient muscle activation, additional positive feedback is presented with video and audio signals. This game can also be played with augmented reality to create the appearance it is in the real world (FIG. 6E) or through virtual reality goggles for the smartphone, such as Google Daydream.

The other games available work in much the same way. First, the EMG signal is detected and the gaming system automatically starts the game at a difficulty level appropriate to the user's ability. Next, the EMG signal is calibrated to move the character between obstacles based on the strength of the signal. As the user progresses and the EMG signals are more controlled, the game begins to move the obstacles closer together to make the user work harder to get more points and pass more levels. This biofeedback in a user friendly form encourages users to continue using the system and does not discourage those that start at a lower ability level.

Figure 9:
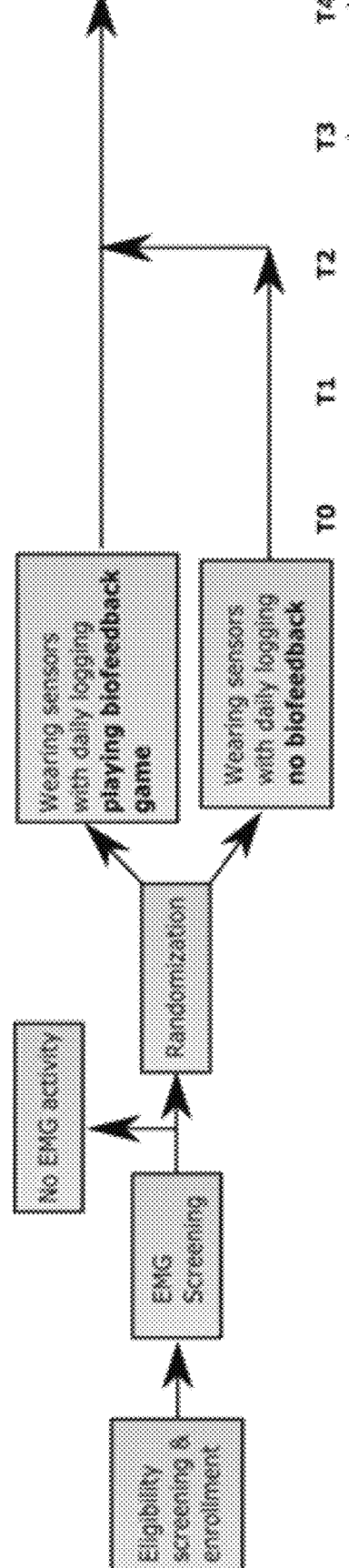
FIG. 9 is a simplified block diagram of a process flow for testing the efficacy of self-dosed biofeedback therapy using the platform of the present inventive disclosure.

Biofeedback games can also be controlled by inertial signals. As users recover enough muscle activation to move joints the games can be controlled by the movement of weak limbs as opposed to the EMG signal. The biofeedback platform 100 was privately tested in a feasibility study where it was shown that a person with spinal cord injury could use the platform 100 to provide self-dosed biofeedback over the course of 60 days. The data uploaded to the cloud also demonstrated improvement in volitional muscle activation over this time (FIG. 6F). It may further be used in a study of its efficacy for enhancing neuroplasticity and muscle recovery in subjects with acute incomplete paraplegia admitted to an inpatient rehabilitation hospital, as depicted in FIG. 9. Subjects must have leg muscles with weak but intact electromyographic activity. The study will be a crossover design with subjects randomize to either begin receiving biofeedback immediately at enrollment or after two weeks. All subjects will be requested to wear the sensors as much as is practical and comfortable, and those randomized to immediate biofeedback will be encouraged to play biofeedback games ad libidum on their smart phone when they have time between therapies. The patients will be assessed at baseline during enrollment and then weekly over the course of four weeks. The measure of maximal volitional electromyographic activity (MVEA) can be compared on a week to week or day to day basis in order to determine how much control the user has of the paretic muscle. The primary outcome will be maximal volitional electromyographic activity they can induce in their weak muscles and how much this improves over two weeks with biofeedback therapy as compared to patients without biofeedback therapy.

Figure 8:
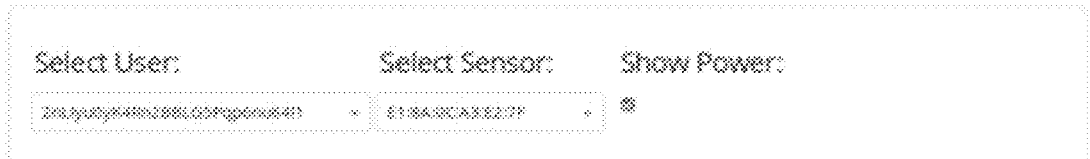
FIG. 8 is an image of an exemplary dashboard depicting data generated by the platform of FIG. 1.
Figure 8:
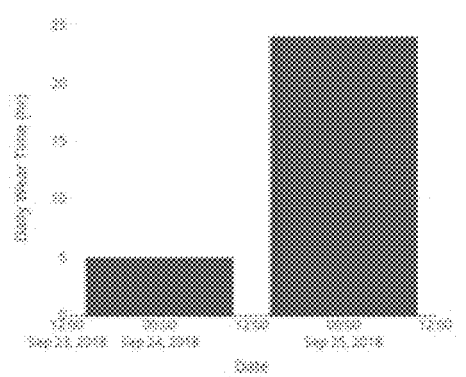
Figure 8:
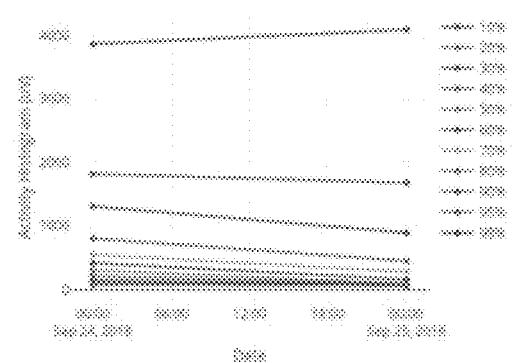
Figure 8:
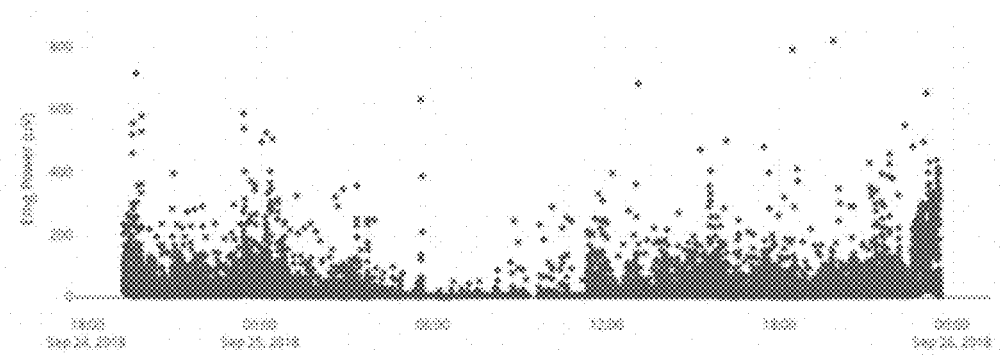

This easily-used, wearable, portable self-dosed biofeedback platform can also be used outside of spinal cord injury. For example, it can be used in stroke patients with spasticity to help relax muscles through the game-based biofeedback, or for people with chronic pain to help with muscle activation. Multiple sensors can also be used to help change patterns of activity such as for people with stroke to move muscles outside of synergy patterns. This can be complemented by providing biofeedback based on the inertial monitoring. The present application offers a system for highly-available electromyographic biofeedback that overcomes many of the barriers to wider utilization of this therapeutic modality, namely cost and ease of use. The system includes an affordable, wearable sensor that provides biofeedback via casual smartphone games, which are controllable by subjects with incomplete paraplegia Returning to FIG. 1, data generated by the sensor device 102 and/or the mobile computing device 104 may then be uploaded to a cloud server and presented on a dashboard for or otherwise made accessible to clinicians, researchers, and therapists to evaluate the user's progress. An exemplary dashboard is depicted in FIG. 8. In one embodiment, data from software executed by the mobile computing device 104 (e.g., a smartphone) is securely transferred to a cloud environment 114 or remote system (e.g., Google Firestore) for monitoring and analysis. The data may be generated system from a home environment and the data fetched or otherwise accessed from the cloud 114 for analysis. In some embodiments, applications executed by the mobile computing device 104 can optimize the Bluetooth bandwidth by only subscribing to the desired characteristics; for example by choosing between either raw IMU data or the internal pose estimate or by selecting either the raw EMG stream versus the onboard power extraction. To optimize power consumption, amplifiers of the sensor device 102 and IMU 208 may be put into a low power mode when there is no subscriber to the corresponding data.

It is contemplated that the IMU 208 may be calibrated to optimize measurements. For example, to obtain a good pose estimate including the heading, it is important to perform an accurate calibration of the magnetometer of the IMU 208. This may involve rotating the sensor device 102 to fully cover all of these possible orientations and then transforming it into a sphere. Other methods may be implemented including ellipsoid fitting to account for hard and soft iron distortions. Calibration settings may be performed or acquired offline for each sensor device 102 used by the platform 100 and then transferred to the sensor device 102 where it may be stored in the flash settings of the device.

The present inventive concept improves upon and addresses technical challenges with respect to traditional laboratory-based outcome measures. Monitoring participants remotely such as at home with wearable sensors is an improvement for rehabilitation. Using the platform 101, it is possible to leave the laboratory and continue monitoring mechanics and activations in a more natural setting. Once freed from the lab there are numerous possible applications including tracking biomechanics as people engage in sport or monitoring gait mechanics via a gaming application or otherwise. The platform 100 further has numerous applications in rehabilitation setting, such as objectively quantifying spasticity or tracking recovery of strength after spinal cord injury. In some embodiments, the platform 101 provides biofeedback with smartphone games to patients with spinal cord injury from EMG-based biofeedback and may include joint angle-based biofeedback.

Exemplary Computing Device

Figure 10:
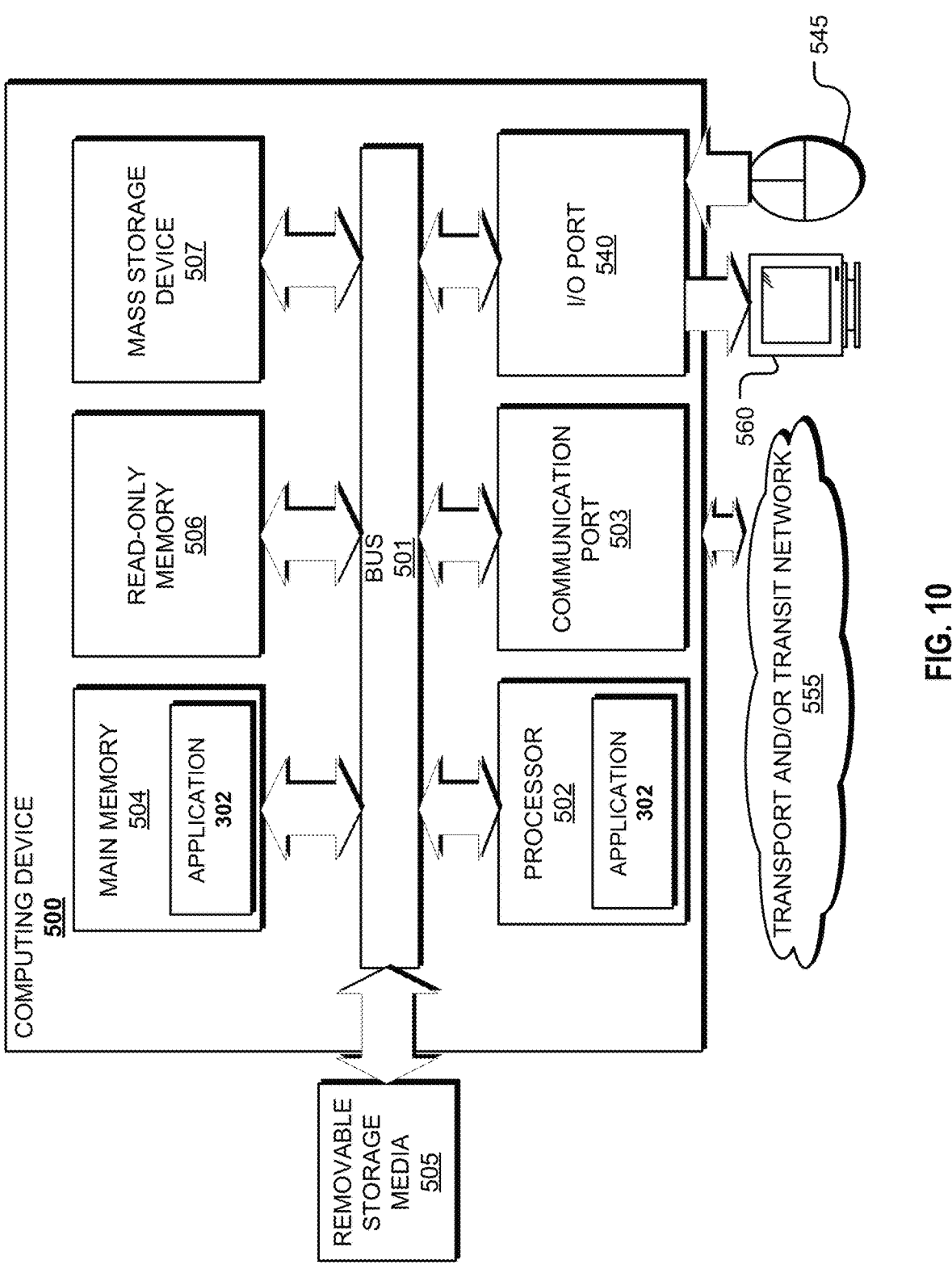
FIG. 10 is an example schematic diagram of a computing device that may implement various methodologies of the exploit prediction framework.

Referring to FIG. 10, a computing device 500 may be used to implement various aspects of the platform 100 described herein. More particularly, in some embodiments, aspects of the platform 100 may be translated to software or machine-level code, which may be installed to and/or executed by the computing device 500 such that the computing device 500 is configured to interpret/display aspects of biofeedback data for therapy and related applications.

It is contemplated that the computing device 500 may include any number of devices, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments, and the like.

The computing device 500 may include various hardware components, such as a processor 502, a main memory 504 (e.g., a system memory), and a system bus 501 that couples various components of the computing device 500 to the processor 502. The system bus 501 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computing device 500 may further include a variety of memory devices and computer-readable media 507 that includes removable/non-removable media and volatile/non-volatile media and/or tangible media, but excludes transitory propagated signals. Computer-readable media 507 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the computing device 500. Communication media includes computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The main memory 504 includes computer storage media in the form of volatile/nonvolatile memory such as read only memory (ROM) and random access memory (RAM). A basic input/output system (BIOS), containing the basic routines that help to transfer information between elements within the computing device 500 (e.g., during start-up) is typically stored in ROM. RAM typically contains data and/or program modules that are immediately accessible to and/or presently being operated on by processor 502. Further, data storage 506 in the form of Read-Only Memory (ROM) or otherwise may store an operating system, application programs, and other program modules and program data.

The data storage 506 may also include other removable/non-removable, volatile/nonvolatile computer storage media. For example, the data storage 506 may be: a hard disk drive that reads from or writes to non-removable, nonvolatile magnetic media; a magnetic disk drive that reads from or writes to a removable, nonvolatile magnetic disk; a solid state drive; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media provide storage of computer-readable instructions, data structures, program modules, and other data for the computing device 500.

A user may enter commands and information through a user interface 540 (displayed via a monitor 560) by engaging input devices 545 such as a tablet, electronic digitizer, a microphone, keyboard, and/or pointing device, commonly referred to as mouse, trackball or touch pad. Other input devices 545 may include a joystick, game pad, satellite dish, scanner, or the like. Additionally, voice inputs, gesture inputs (e.g., via hands or fingers), or other natural user input methods may also be used with the appropriate input devices, such as a microphone, camera, tablet, touch pad, glove, or other sensor. These and other input devices 545 are in operative connection to the processor 502 and may be coupled to the system bus 501, but may be connected by other interface and bus structures, such as a parallel port, game port or a universal serial bus (USB). A monitor 560 or other type of display device may also be connected to the system bus 501. The monitor 560 may also be integrated with a touch-screen panel or the like.

The computing device 500 may be implemented in a networked or cloud-computing environment using logical connections of a network interface 503 to one or more remote devices, such as a remote computer. The remote computer may be a personal computer, a server, a router, a network PC, a peer device or other common network node, and typically includes many or all of the elements described above relative to the computing device 500. The logical connection may include one or more local area networks (LAN) and one or more wide area networks (WAN), but may also include other networks. Such networking environments are commonplace in offices, enterprise-wide computer networks, intranets and the Internet.

When used in a networked or cloud-computing environment, the computing device 500 may be connected to a public and/or private network through the network interface 503. In such embodiments, a modem or other means for establishing communications over the network is connected to the system bus 501 via the network interface 503 or other appropriate mechanism. A wireless networking component including an interface and antenna may be coupled through a suitable device such as an access point or peer computer to a network. In a networked environment, program modules depicted relative to the computing device 500, or portions thereof, may be stored in the remote memory storage device.

Certain embodiments are described herein as including one or more modules. Such modules are hardware-implemented, and thus include at least one tangible unit capable of performing certain operations and may be configured or arranged in a certain manner. For example, a hardware-implemented module may comprise dedicated circuitry that is permanently configured (e.g., as a special-purpose processor, such as a field-programmable gate array (FPGA) or an application-specific integrated circuit (ASIC)) to perform certain operations. A hardware-implemented module may also comprise programmable circuitry (e.g., as encompassed within a general-purpose processor or other programmable processor) that is temporarily configured by software or firmware to perform certain operations. In some example embodiments, one or more computer systems (e.g., a stand-alone system, a client and/or server computer system, or a peer-to-peer computer system) or one or more processors may be configured by software (e.g., an application or application portion) as a hardware-implemented module that operates to perform certain operations as described herein.

Accordingly, the term "hardware-implemented module" encompasses a tangible entity, be that an entity that is physically constructed, permanently configured (e.g., hard-wired), or temporarily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software may accordingly configure the processor 502, for example, to constitute a particular hardware-implemented module at one instance of time and to constitute a different hardware-implemented module at a different instance of time.

Hardware-implemented modules may provide information to, and/or receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses) that connect the hardware-implemented modules. In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation, and may store the output of that operation in a memory device to which it is communicatively coupled. A further hardware-implemented module may then, at a later time, access the memory device to retrieve and process the stored output. Hardware-implemented modules may also initiate communications with input or output devices.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system, comprising:
   one or more wearable sensor devices configured to engage skin tissue proximate to a muscle of a user and generate signal data resulting from activity of the muscle, the one or more wearable sensor devices including at least one inertial measurement unit (IMU) and at least one electromyogram (EMG) sensor, wherein the IMU includes at least one magnetometer, at least one gyroscope, and at least one accelerometer;
   a processor in operative communication with the one or more wearable sensor devices, wherein the processor is configured for processing electromyography data and inertial data defined by the signal data, and wherein the processor is integrated along the one or more wearable sensor devices and is configured to measure a joint rotation angle about a hinge joint axis while compensating for multi-axial human joint rotation, wherein the processor:
      constructs, based on quaternion pose signal data from the one or more wearable sensor devices, a rotation vector incorporating a unit norm of the quaternion pose signal data,
      projects the rotation vector along a first principal component representative of the hinge joint axis of rotation as a unit norm vector, and
      measures the joint rotation angle about the hinge joint axis based on a length of the rotation vector following projection; and
   a mobile game executable by a mobile device in operative communication with the processor, wherein the mobile game configures the mobile device for executing instructions including:
      receiving the electromyography data and the inertial data of the signal data;
      executing an instance of a game program, wherein the electromyography data and inertial data are taken as input to the game program in real-time;
      mapping a set of qualities of the electromyography data to one or more user inputs based on one or more relationships between the set of qualities of the electromyography data and the one or more user inputs, wherein the set of qualities of the electromyography data comprise timing and intensity of muscle activation;
      applying the one or more user inputs to the game program to create an updated state of the game program;
      displaying the updated state of the game program to provide the user with real-time biofeedback based on the electromyography data; and
      adjusting a difficulty of the game program by modifying the one or more relationships between the set of qualities of the electromyography data and the one or more user inputs based on the signal data.

2. The system of claim 1, wherein the one or more wearable sensor devices are configured to topically adhere to a paretic muscle of the user.

3. The system of claim 1, wherein the one or more wearable sensor devices record the signal data throughout a day.

4. The system of claim 1, wherein the one or more wearable sensor devices are operable for storing the signal data.

5. The system of claim 1, wherein the inertial measurement unit generates magnetometer data including a directional heading.

6. The system of claim 1, wherein the electromyography data and the inertial data are communicated to the mobile device using Bluetooth.

7. The system of claim 1, wherein the game program prompts the user to repeat certain behaviors to help recovery or provide self-dosed therapy.

8. The system of claim 1, wherein the one or more wearable sensor devices are operable to stream the signal data to the mobile device.

9. The system of claim 1, further comprising:

a cloud in operable communication with the mobile device, wherein aspects of the signal data pertaining to user activity collected by the mobile device is logged in the cloud; and a user interface implemented by the mobile device, wherein the user interface displays data pertaining to user activity, wherein the data pertaining to user activity comprises the signal data collected by the wearable sensor devices, a set of user gameplay performance statistics, and a set of user gameplay time data.

10. The system of claim 9, further comprising:

a virtual reality system in operable communication with the processor, wherein the virtual reality system displays the user interface.

11. The system of claim 1, wherein applying the one or more user inputs to the game program to create an updated state of the game program comprises affecting a user action within the game program based on the one or more user inputs.

12. The system of claim 1, wherein the processor is further configured to measure a gyroscopic rotation rate about the hinge joint axis by transforming gyroscopic rotation rate signals obtained by the one or more wearable sensor devices along the first principal component.

13. The system of claim 12, wherein the processor is further configured to:

evaluate a rate of change of the joint rotation angle about the hinge joint axis between a first time step and a second time step;

evaluate a gyroscopic rotation difference between the gyroscopic rotation rate about the hinge joint axis at the first time step and the gyroscopic rotation rate about the hinge joint axis at the second time step; and measure consistency between the one or more wearable sensor devices based on a comparison between the rate of change of the joint rotation angle about the hinge joint axis and the gyroscopic rotation difference.

14. The system of claim 1, wherein the processor is further configured to:

measure a baseline attitude of each of the one or more wearable sensor devices with the user's joint at a neutral position; and remove a baseline attitude vector from subsequent attitude vector measurements such that a joint angle vector is correct relative to positions of each of the one or more wearable sensor devices.

15. A method, comprising:

receiving, by a processor, electromyography data representing electrical signals resulting from muscle activation by a user;

receiving, by the processor, inertial data representing movement or spatial orientation of a plurality of inertial sensors associated with the user, wherein the inertial data comprises accelerometer data, gyroscope data, and magnetometer data;

measuring, by the processor, using the accelerometer data, the gyroscope data, and the magnetometer data, a joint rotation angle about a hinge joint axis while compensating for multi-axial human joint rotation by:

constructing based on quaternion pose signal data from the one or more wearable sensor devices, a rotation vector incorporating a unit norm of the quaternion pose signal data, projecting the rotation vector along a first principal component representative of the hinge joint axis of rotation as a unit norm vector, and measuring the joint rotation angle about the hinge joint axis based on a length of the rotation vector following projection;

updating, by the processor, an attitude vector associated with each inertial sensor using the accelerometer data, the gyroscope data, and the magnetometer data, wherein gyroscopic drift is compensated for by using a set of measured accelerometer and magnetometer data and a set of predicted accelerometer and magnetometer data;

determining, by the processor, a joint angle vector between two inertial sensors of the plurality of inertial sensors using attitude vectors associated with the two inertial sensors, wherein a baseline attitude vector for each of the two inertial sensors is used to establish relativity between the two inertial sensors;

determining, by the processor, a rotation rate around a joint axis defined by the joint angle vector; and controlling actions in an experience presented to the user based on timing and intensity of muscle activation of the user and one or more of the electromyography data, the attitude vector for each inertial sensor, the joint angle vector between the two inertial sensors, or the rotation rate around the joint axis.

16. The method of claim 15, further comprising:

measuring a baseline attitude of each inertial sensor with the user's joint at a neutral position and removing the baseline attitude vector from subsequent attitude vector measurements such that the joint angle vector is correct relative to the positions of each of the inertial sensors.

17. The method of claim 15, wherein the magnetometer data comprises a directional heading.

18. The method of claim 15, wherein the electromyography data and the inertial data are communicated to the processor using Bluetooth.

19. The method of claim 15, wherein the processor communicates the electromyography data, the attitude vector for each inertial sensor, the joint angle vector between two inertial sensors, or the rotation rate around the joint axis to a cloud database or a mobile device using Bluetooth.

20. A tangible, non-transitory, computer-readable medium having instructions encoded thereon, the instructions, when executed by a processor, being operable to:

access electromyography data representing electrical signals resulting from muscle manipulation including amplitude and timing of a muscle contraction by a user associated with at least one wearable sensor device;

access inertial data representing movement or spatial orientation associated with the at least one wearable sensor device, wherein the inertial data comprises accelerometer data, gyroscope data, and magnetometer data;

map a set of qualities of the electromyography data to actions of the user in a gaming experience, wherein the set of qualities of the electromyography data comprise timing and intensity of muscle activation;

control actions of the user in the gaming experience based on the set of qualities of the electromyography data; and measure, using the accelerometer data, the gyroscope data, and the magnetometer data, a joint rotation angle about a hinge joint axis while compensating for multi-axial human joint rotation by: constructing, based on quaternion pose signal data from the wearable sensor device, a rotation vector incorporating a unit norm of the quaternion pose signal data; projecting the rotation vector along a first principal component representative of the hinge joint axis of rotation as a unit norm vector; and measuring the joint rotation angle about the hinge joint axis based on a length of the rotation vector following projection.

21. The tangible, non-transitory, computer-readable medium of claim 20, having further instructions encoded thereon, the further instructions, when executed by the processor, being operable to:

update an attitude vector using the accelerometer data, the gyroscope data, and the magnetometer data, wherein gyroscopic drift is compensated for by using a set of measured accelerometer and magnetometer data and a set of predicted accelerometer and magnetometer data;

determine a joint angle vector using attitude vectors, wherein a baseline attitude vector is used to establish relativity;

determine a rotation rate around a joint axis defined by the joint angle vector; and modify the gaming experience presented to the user based on one or more of the electromyography data, the attitude vector, the joint angle vector, or the rotation rate around the joint axis.

22. The tangible, non-transitory, computer-readable medium of claim 18, having further instructions encoded thereon, the further instructions, when executed by the processor, being operable to:

measure a gyroscopic rotation rate about the hinge joint axis by transforming gyroscopic rotation rate signals obtained by the at least one wearable sensor device along the first principal component.

23. The tangible, non-transitory, computer-readable medium of claim 22, having further instructions encoded thereon, the further instructions, when executed by the processor, being operable to:

evaluate a rate of change of the joint rotation angle about the hinge joint axis between a first time step and a second time step;

evaluate a gyroscopic rotation difference between the gyroscopic rotation rate about the hinge joint axis at the first time step and the gyroscopic rotation rate about the hinge joint axis at the second time step; and measure accuracy of the at least one wearable sensor device based on a comparison between the rate of change of the joint rotation angle about the hinge joint axis and the gyroscopic rotation difference.

24. The tangible, non-transitory, computer-readable medium of claim 20, having further instructions encoded thereon, the further instructions, when executed by the processor, being operable to:

measure a baseline attitude of each of the at least one wearable sensor device with the user's joint at a neutral position; and remove a baseline attitude vector from subsequent attitude vector measurements such that a joint angle vector is correct relative to positions of each of the at least one wearable sensor device.

\* \* \* \* \*